(12) United States Patent
Tiedemann et al.

(10) Patent No.: US 8,822,440 B2
(45) Date of Patent: Sep. 2, 2014

(54) INHIBITING CYCLIN D POLYPEPTIDES

(75) Inventors: Rodger E. Tiedemann, Scottsdale, AZ (US); Alexander Keith Stewart, Scottsdale, AZ (US); Aaron David Schimmer, Thornhill (CA); Xinliang Mao, Markham (CA)

(73) Assignees: Mayo Foundation for Medical Education and Research, Rochester, MN (US); University Health Network, Toronto (CA)

( * ) Notice: Subject to any disclaimer, the term of this patent is extended or adjusted under 35 U.S.C. 154(b) by 1542 days.

(21) Appl. No.: 12/445,065

(22) PCT Filed: Oct. 10, 2007

(86) PCT No.: PCT/US2007/080978
§ 371 (c)(1),
(2), (4) Date: Feb. 15, 2010

(87) PCT Pub. No.: WO2008/045955
PCT Pub. Date: Apr. 17, 2008

(65) Prior Publication Data
US 2010/0144685 A1   Jun. 10, 2010

Related U.S. Application Data

(60) Provisional application No. 60/850,567, filed on Oct. 10, 2006.

(51) Int. Cl.
| A61K 31/573 | (2006.01) |
| A61K 31/56 | (2006.01) |
| A61K 31/352 | (2006.01) |
| G01N 33/68 | (2006.01) |
| C07K 14/47 | (2006.01) |
| G01N 33/566 | (2006.01) |
| A61K 38/00 | (2006.01) |

(52) U.S. Cl.
CPC ............... *A61K 31/352* (2013.01); *A61K 31/56* (2013.01); *A61K 38/00* (2013.01); *G01N 33/6872* (2013.01); *A61K 31/573* (2013.01); *C07K 14/4738* (2013.01); *G01N 33/566* (2013.01)
USPC ...................... 514/171; 435/372.1

(58) Field of Classification Search
CPC .................................................... A61K 31/352
USPC .......................................... 514/171; 435/375
See application file for complete search history.

(56) References Cited

U.S. PATENT DOCUMENTS

| 5,151,425 | A | 9/1992 | Clark |
| 5,164,394 | A | 11/1992 | Bolund et al. |
| 6,444,233 | B1 | 9/2002 | Arntzen et al. |
| 6,462,041 | B1 | 10/2002 | Cai et al. |
| 6,613,762 | B2 | 9/2003 | Cai et al. |
| 6,689,398 | B2 | 2/2004 | Haridas et al. |
| 6,746,696 | B2 | 6/2004 | Arntzen et al. |
| 6,962,720 | B2 | 11/2005 | Haridas et al. |
| 2004/0082066 | A1* | 4/2004 | Cai et al. ................. 435/375 |
| 2004/0086580 | A1 | 5/2004 | Tripp et al. |
| 2004/0127470 | A1 | 7/2004 | Masferrer |
| 2004/0151792 | A1 | 8/2004 | Tripp et al. |
| 2004/0220267 | A1 | 11/2004 | Devlin |
| 2005/0008717 | A1 | 1/2005 | Einbond et al. |
| 2005/0054620 | A1* | 3/2005 | Koeffler et al. ............ 514/167 |
| 2005/0197405 | A1* | 9/2005 | Li et al. .................. 514/680 |
| 2005/0261363 | A1 | 11/2005 | Lee et al. |

FOREIGN PATENT DOCUMENTS

| WO | WO2005046731 A1 | 5/2005 |
| WO | WO2005060663 A2 | 7/2005 |
| WO | WO2005073164 A1 | 8/2005 |
| WO | WO2005020892 B1 | 12/2005 |

OTHER PUBLICATIONS

Ishi et al., Cell Growth & Differentiation, vol. 13, p. 19-26, 2002.*
Wang et al. (Leukemia & Lymphoma, vol. 43, No. 9, p. 1827-1835, 2002).*
Athanasiou et al., American Journal of Clinical Pathology, vol. 116, p. 535-542, 2001.*
Hornung et al. (Cancer Research, vol. 52, p. 101-107, 1992).*
"Living with Multiple Myeloma" website (<http://multiplemyelomablog.com>, accessed Aug. 7, 2013).*
"NTP Toxicology and Carcinogenesis Studies of C.I. Basic Red 9 Monohydrochloride (Pararosaniline) (CAS No. 569-61-9) in F344/N Rats and B6C3F1 Mice (Feed Studies)," Natl Toxicol Program Tech Rep Ser, 1986, 285:1-228.
Abraham et al., "Functional gene expression analysis of clonal plasma cells identifies a unique molecular profile for light chain amyloidosis," Blood, 2005, 105(2):794-803.
Arafat and Musa, "Patulin-induced inhibition of protein synthesis in hepatoma tissue culture," Res Commun Mol Pathol Pharmacol, 1995, 87(2):177-186.
Ashurst et al., "The Vertebrate Genome Annotation (Vega) database," Nucleic Acids Res, 2005, 33(Database issue):D459-D465.
Au et al., "Further study of the genetic toxicity of gentian violet," Mutat Res, 1979, 66(2):103-112.
Bartsch et al., "Acute toxicity of various solvents in the mouse and rat. LD50 of ethanol, diethylacetamide, dimethylformamide, dimethylsulfoxide, glycerine, N-methylpyrrolidone, polyethylene glycol 400, 1,2-propanediol and Tween 20," Drug Research, 1976, 26(8):1581-1583.
Becci et al., "Long-term carcinogenicity and toxicity studies of patulin in the rat," J Appl Toxicol,1981, 1(5):256-261.

(Continued)

*Primary Examiner* — Susan Hanley
*Assistant Examiner* — Damon B Bowe
(74) *Attorney, Agent, or Firm* — Fish & Richardson P.C.

(57) ABSTRACT

This document involves methods and materials related to inhibiting cyclin D polypeptide activity. For example, this document provides methods and materials that can be used to (1) identify mammals or cells in need of cyclin D polypeptide inhibition and (2) administer an agent capable of inhibiting cyclin D polypeptide activity.

10 Claims, 26 Drawing Sheets

(56) References Cited

OTHER PUBLICATIONS

Bergsagel et al., "Cyclin D dysregulation: an early and unifying pathogenic event in multiple myeloma," Blood, 2005, 106(1):296-303.
Birney et al., "Ensembl 2006," Nucleic Acids Res., 2006, 34(Database issue):D556-D561.
Brooks et al., "Functional Analysis of the Human Cyclin D2 and Cyclin D3 Promoters," J Biol Chem, 1996, 271 (15):9090-9099.
Burghardt et al., "Patulin-induced cellular toxicity: a vital fluorescence study," Toxicol Appl Pharmacol, 1992, 112 (2):235-244.
Chang et al., "Antitumor agents. 228. five new agarofurans, Reissantins A-E, and cytotoxic principles from Reissantia buchananii," J Nat Prod, 2003, 66:1416-1420.
Coley et al., "Further examination of 9-alkyl- and sugar-modified anthracyclines in the circumvention of multidrug resistance," Anticancer Drug Des, 1992, 7(6):471-481.
Del Bino and Darzynkiewicz, "Camptothecin, teniposide, or 4'-(9-acridinylamino)-3-methanesulfon-m-anisidide, but not mitoxantrone or doxorubicin, induces degradation of nuclear DNA in the S phase of HL-60 cells," Cancer Res, 1991, 51(4):1165-1169.
Docampo and Moreno, "The metabolism and mode of action of gentian violet," Drug Metab Rev, 1990, 22 (2-3):161-178.
Gray, "Hormonal regulation of plant growth and development," PLoS Biol, 2004, 2(9):1270-1273.
Griffaut et al., "Cytotoxic effects of kinetin riboside on mouse, human and plant tumour cells," Int J Biol Macromol, 2004, 34(4):271-275.
Guo et al., "General gambogic acids inhibited growth of human hepatoma SMMC-7721 cells in vitro and in nude mice," Acta Pharmacol Sin, 2004, 25(6):769-774.
Guo et al., "Inhibition of human telomerase reverse transcriptase gene expression by gambogic acid in human hepatoma SMMC-7721 cells," Life Sciences, 2006, 78(11):1238-1245.
Hennequin et al., "Interaction of Ionizing Radiation with the Topoisomerase I Poison Camptothecin in Growing V-79 and HeLa Cells," Cancer Res., 1994, 54:1720-1728.
Honma and Ishii, "Differentiation of human myeloid leukemia cells by plant redifferentiation-inducing hormones," Leuk Lymphoma, 2002, 43(9):1729-1735.
Ishii et al., "Control of differentiation and apoptosis of human myeloid leukemia cells by cytokinins and cytokinin nucleosides, plant redifferentiation-inducing hormones," Cell Growth Differ, 2002, 13:19-26.
Jourdan et al., "The myeloma cell antigen syndecan-1 is lost by apoptotic myeloma cells," Br J Haematol, 1998, 100:637-646.
Kasibhatla et al., "A role for transferring receptor in triggering apoptosis when targeted with gambogic acid," Proc Natl Acad Sci USA, 2005, 102(34):12095-12100.
Kozar et al., "Mouse development and cell proliferation in the absence of D-cyclins," Cell, 2004, 118(4):477-491.
Krajewski et al., "Detection of multiple antigens on western blots," Anal Biochem, 1996, 236:221-228.
Krivobok et al., "Antitumoral activity of patulin and patulin-cysteine adducts," Pharmazie,1994, 49(4):277-279.
Liu et al., "Anticancer effect and apoptosis induction of gambogic acid in human gastric cancer line BGC-823," World J Gastroenterol, 2005, 11(24):3655-3659.
Mao et al., "A High Throughput Seeking Myeloma Therapeutics Identifies Glucocorticoids as Inhibitors of c-Maf-Dependent Transactivation of Cyclin D2," Blood, (ASH Annual Meeting Abstracts), 2005,106:Abstract 3384.
Marin et al., "Effects of mycotoxins on cytokine production and proliferation in EL-4 thymoma cells," J Toxicol Environ Health, 1996, 48(4):379-396.
Niampoka et al., "Potentially cytotoxic triterpenoids from the root bark of Siphonodon celastrineus Griff," Arch Pharm Res, 2005, 28:546-549.
Osswald et al., "Long-term testing of patulin administered orally to Sprague-Dawley rats and Swiss mice," Food Cosmet Toxicol, 1978, 16(3):243-247.
Parker and Binder, "Gentian violet keratoconjunctivitis," Am J Ophthalmol, 1979, 87:340-343.
Pestka and Bondy, "Alteration of immune function following dietary mycotoxin exposure," Can J Physiol Pharmacol, 1990, 68(7):1009-1016.
Rihn et al., "Morphological alterations induced by patulin on cultured hepatoma cells," Arch Toxicol, 1986, (suppl 9):275-278.
Riou-Khamlichi et al., "Cytokinin Activation of Arabidopsis Cell Division Through a D-Type Cyclin," Science, 1999, 283:1541-1544.
Schmülling, "New Insights into the Functions of Cytokinins in Plant Development," J Plant Growth Regul, 2002, 21:40-49.
Seigle-Murandi et al., "Antitumor activity of patulin and structural analogs," Pharmazie, 1992, 47(4):288-291.
Shao et al., "Abrogation of an S-phase checkpoint and potentiation of camptothecin cytotoxicity by 7-hydroxystaurosporine (UCN-01) in human cancer cell lines, possibly influenced by p53 function," Cancer Res, 1997, 57 (18):4029-4035.
Shim et al., "Bach2 is involved in neuronal differentiation of N1E-115 neuroblastoma cells," Experimental Cell Research, 2006, 312(12):2264-2278.
Werner et al., "Regulation of plant growth by cytokinin," Proc Natl Acad Sci USA, 2001, 98(18):10487-10492.
Wu et al., "Gambogic acid inhibits proliferation of human lung carcinoma SPC-A1 cells in vivo and in vitro and represses telomerase activity and telomerase reverse transcriptase mRNA expression in the cells," Biol Pharm Bull, 2004, 27(11):1769-1774.
Wu et al., "Pristimerin induces caspase-dependent apoptosis in MDA-MB-231 cells via direct effects on mitochondria," Molyu Cancer Ther, 2005, 4(8):1277-1285.
Yu et al., "Repression of telomerase reverse transcriptase mRNA and hTERT promoter by gambotic acid in human gastric carchinoma cells," Cancer Chemother Pharmacol, 2006, 58(4):434-443.
Zhang et al., "Discovery, characterization and SAR of gambogic acid as a potent apoptosis inducer, by a HTS assay," Bioorg Med Chem, 2004, 12(2):309-317.
Zhao et al., "Gambogic acid induces apoptosis and regulates expressions of Bax and Bcl-2 protein in human gastric carcinoma MGC-803 cells," Biol Pharm Bull, 2004, 27(7):998-1003.
Authorized Officer Weon Hye Shin, Declaration of Non-Establishment of International Search Report and Written Opinion of the International Searching Authority in PCT/US2007/80987 mailed Jun. 11, 2008, 4 pages.
Authorized Officer Nora Lindner, International Preliminary Report on Patentability in PCT/US2007/80987 mailed Apr. 15, 2009, 4 pages.

\* cited by examiner

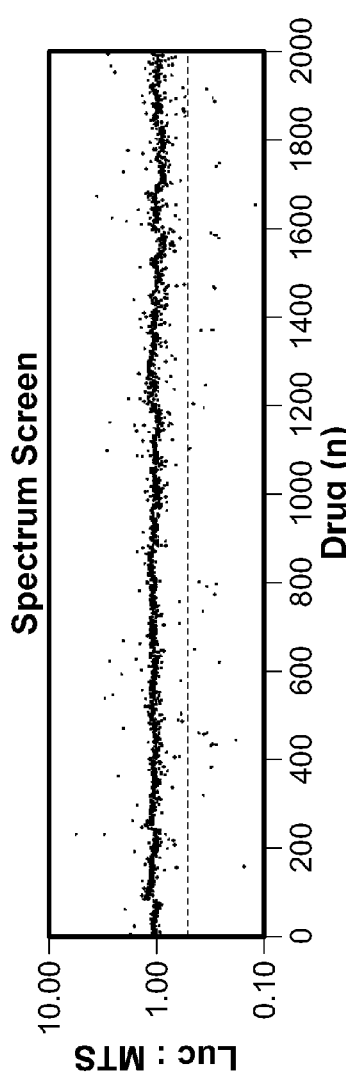
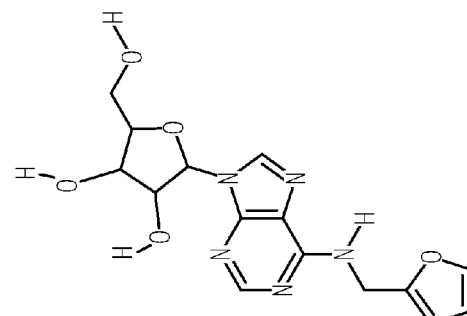
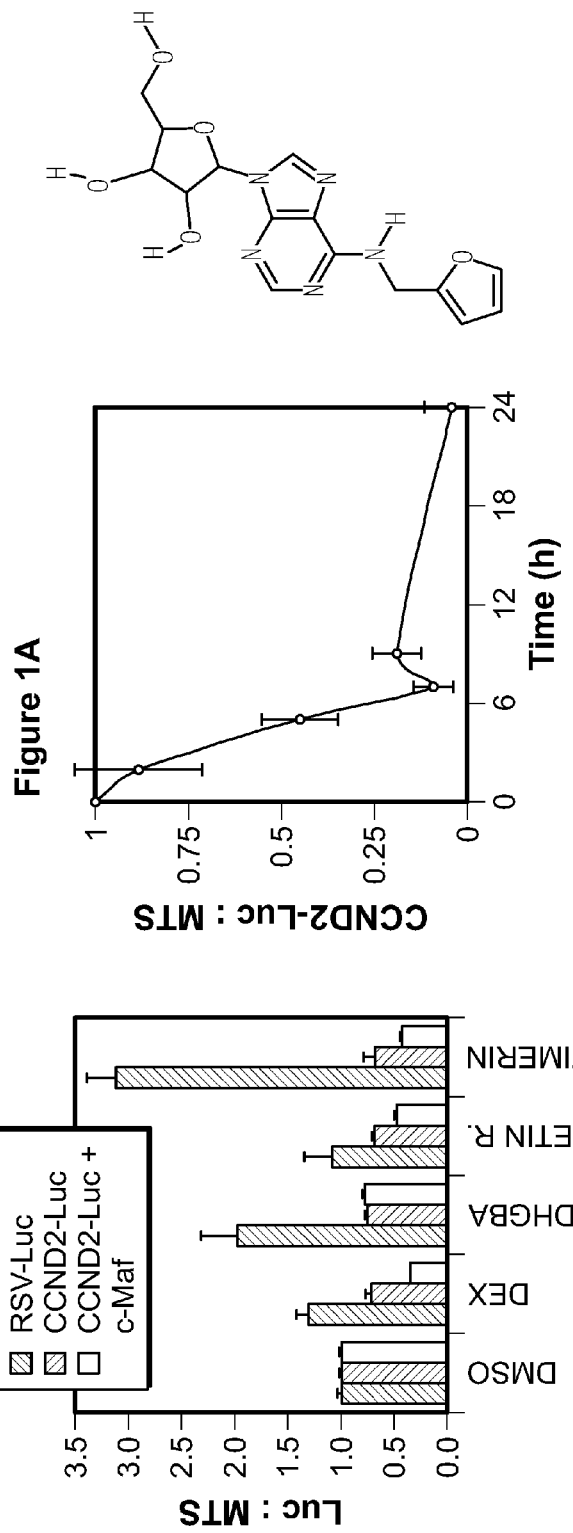
Figure 1A
Figure 1B
Figure 1C
Figure 1D

Affymetrix Probes

| Hg_U133_plus2 probe | Relative mRNA Expression after Kinetin Riboside Treatment* | | CREM Transcript Variant(s) Targeted by Probe† | Interpretation |
|---|---|---|---|---|
| | H929 | U266 | | |
| 228092_at | 1.04 | 1.14 | 002, 008 | Not Induced |
| 210171_s_at | 1.09 | 1.04 | 004, 006, 009, 015, 016 | Not Induced |
| 207630_s_at | 3.18 | 4.88 | 003, 005, *006*, 010, 011, *012* | At Least one: 003, 005, 010, 011, 012 Induced |
| 214508_x_at | 3.18 | 2.65 | *001*, 003, 004, 005, *006*, *009*, 010, 011 | At Least one: 003, 005, 010, 011 Induced |
| 209967_s_at | 3.12 | 5.41 | *001*, 003, *004*, *009* | 003 Induced |
| 230511_at | 1.23 | 1.14 | *001*, *004*, *009* | Not Induced |

\* Expression of probe set target mRNA sequences was quantified by GEP 4 hours after treatment and is depicted as the normalized ratio of expression levels in Kinetin riboside-treated cells to DMSO-treated cells † *CREM* variants in italics are potential targets of the indicated probe but are also targets of other probes that show no induced expression

Figure 7C

| CREM Variant | Name | Function |
|---|---|---|
| 003 (019) NM_183013.1 | hCREM type 1 Alpha | Type Alpha Repressor Isoform |
| 005 | ICER11 Gamma and hCREM 2beta-b, CREM Isoform e | Early Repressor ICER Isoform |
| 010 | CREM Isoform j | Early Repressor ICER Isoform |
| 011 | CREM Isoform k | Early Repressor ICER Isoform |
| 012 | CREM Isoform l | Early Repressor ICER Isoform |

Figure 7D

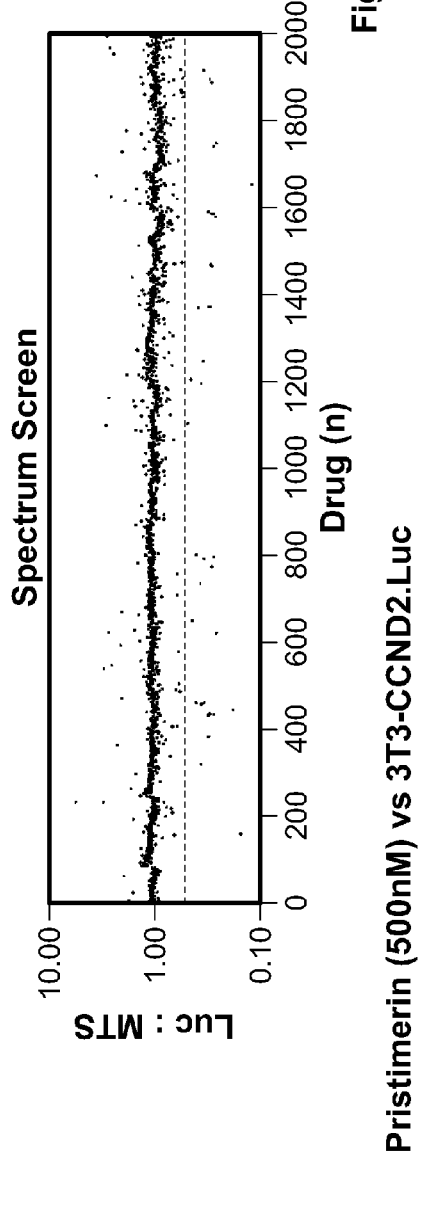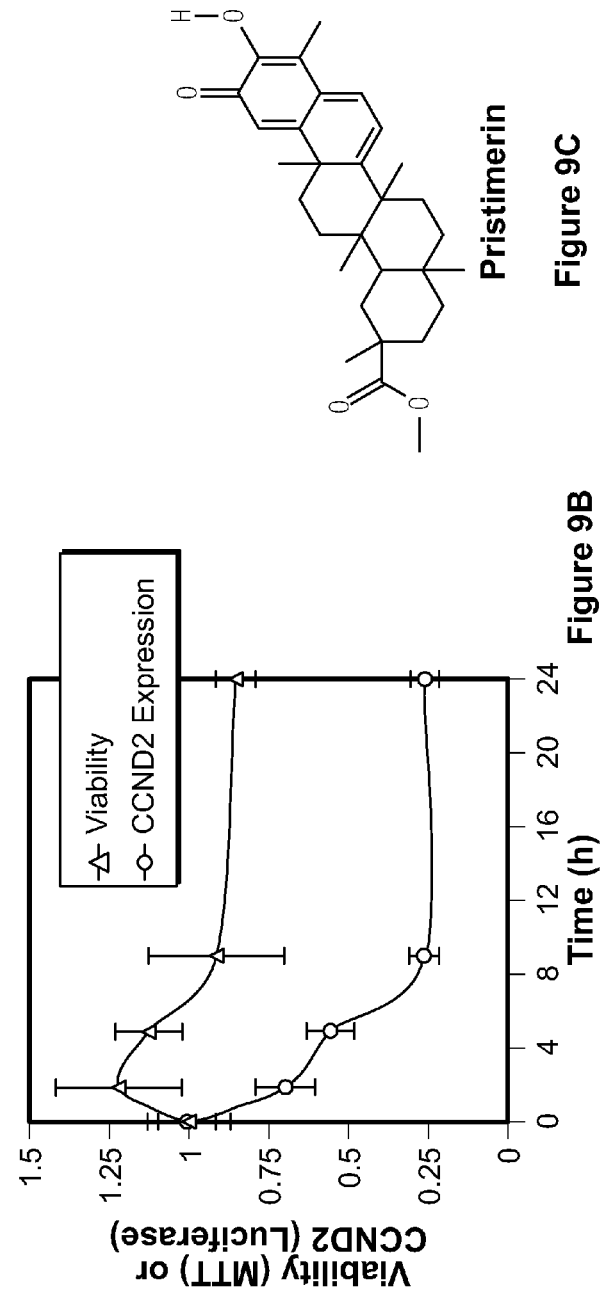
Figure 9A
Figure 9B
Figure 9C

Pat 11 BM+DMSO 96h.001

| Quad | Events | % Gated | % Total | X Mean | Y Mean |
|---|---|---|---|---|---|
| UL | 117 | 3.22 | 3.22 | 27.28 | 498.64 |
| UR | 35 | 0.96 | 0.96 | 1377.79 | 766.86 |
| LL | 1653 | 45.45 | 45.45 | 34.98 | 6.59 |
| LR | 1832 | 50.37 | 50.37 | 1160.60 | 3.74 |

Pat 11 BM+Primist 0.1µM 96h.001

| Quad | Events | % Gated | % Total | X Mean | Y Mean |
|---|---|---|---|---|---|
| UL | 19 | 0.56 | 0.56 | 83.26 | 391.47 |
| UR | 34 | 0.99 | 0.99 | 1369.42 | 486.24 |
| LL | 1257 | 36.72 | 36.72 | 46.44 | 7.04 |
| LR | 2113 | 61.73 | 61.73 | 997.22 | 3.99 |

INHIBITING CYCLIN D POLYPEPTIDES

CROSS REFERENCE RELATED APPLICATIONS

This application is a National Stage application under 35 U.S.C. §371 and claims benefit under 35 U.S.C. §119(a) of International Application No. PCT/US2007/080978 having an International Filing Date of Oct. 10, 2007, which claims the benefit priority to U.S. Provisional Application Ser. No. 60/850,567, filed on Oct. 10, 2006, the contents of which are herein incorporated by reference in their entirety.

BACKGROUND

1. Technical Field

This document relates to methods and materials involved in inhibiting cyclin D polypeptides. For example, this document provides methods and materials for using kinetin riboside or pristimerin to inhibit cyclin D polypeptide activity by inhibiting, e.g., the expression of nucleic acid encoding a cyclin D polypeptide.

2. Background Information

There are about 1.2 million new cancer cases and about 600,000 deaths per year from cancer in the United States. If chemotherapy were completely effective, most of these cancer deaths could be avoided. The high mortality rate from cancer highlights the need for improved therapy.

SUMMARY

This document involves methods and materials related to inhibiting cyclin D polypeptide activity by inhibiting, for example, the expression of nucleic acid encoding a cyclin D polypeptide. For example, this document provides methods and materials that can be used to (1) identify mammals or cells in need of cyclin D polypeptide inhibition and (2) administer an agent capable of inhibiting cyclin D polypeptide activity. Inhibiting cyclin D polypeptide activity as described herein can be used to help treat cancer such as multiple myeloma, non-Hodgkins lymphoma, breast cancer, and other cancers that depend on cyclin D.

In general, this document features a method for reducing cyclin D polypeptide activity within a cell. The method comprises, or consists essentially of: (a) identifying a cell in need of reduced cyclin D polypeptide activity, and (b) administering an agent to the cell, wherein the agent is monensin, patulin, β-lapachone, camptothecin, dihydrogambogic acid, gentian violet, thapsigargin, brefeldin A, pristimerin, or kinetin riboside. The cell can be a myeloma cell. The agent can be kinetin riboside. The method can comprise administering a combination of at least two agents selected from the group consisting of monensin, patulin, β-lapachone, camptothecin, dihydrogambogic acid, gentian violet, thapsigargin, brefeldin A, pristimerin, and kinetin riboside. The method can comprise administering kinetin riboside and a glucocorticosteroid to the cell. The glucocorticosteroid can be dexamethasone.

In another aspect, this document features a method for treating a mammal having a cancer (e.g., myeloma). The method comprises, or consists essentially of, administering kinetin riboside and a glucocorticosteroid to the mammal. The mammal can be a human. The cancer (e.g., myeloma) can be multiple myeloma. The glucocorticosteroid can be dexamethasone.

In another aspect, this document features a method for reducing the number or proliferation of viable cancer cells within a mammal. The method comprises, or consists essentially of: (a) identifying a mammal having viable cancer cells in need of reduced cyclin D polypeptide activity, and (b) administering an agent to the mammal under conditions wherein the number of viable cancer cells within the mammal is reduced, wherein the agent is monensin, patulin, β-lapachone, camptothecin, dihydrogambogic acid, gentian violet, thapsigargin, brefeldin A, pristimerin, kinetin riboside, or a combination thereof. The viable cancer cells can be myeloma cells. The mammal can be a human. The agent can be kinetin riboside. The method can comprise administering kinetin riboside and a glucocorticosteroid to the mammal. The glucocorticosteroid can be dexamethasone.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 9. Screening of the Spectrum library for inhibitors of CCND2 transactivation. (A) Dot plot of the Spectrum library of 2000 drugs and natural compounds and their effects on CCND2 promoter transactivation (measured by luciferase assay) relative to NIH3T3 viability (MTS). The Lopac and Prestwick drug libraries were also screened but are not shown. (B) Time course of pristimerin-mediated suppression of CCND2-driven luciferase in NIH3T3. This shows the relatively minor effects of pristimerin on fibroblast viability despite inducing rapid and considerable suppression of CCND2. (C) Chemical structure of pristimerin.

DETAILED DESCRIPTION

Figure 2A:
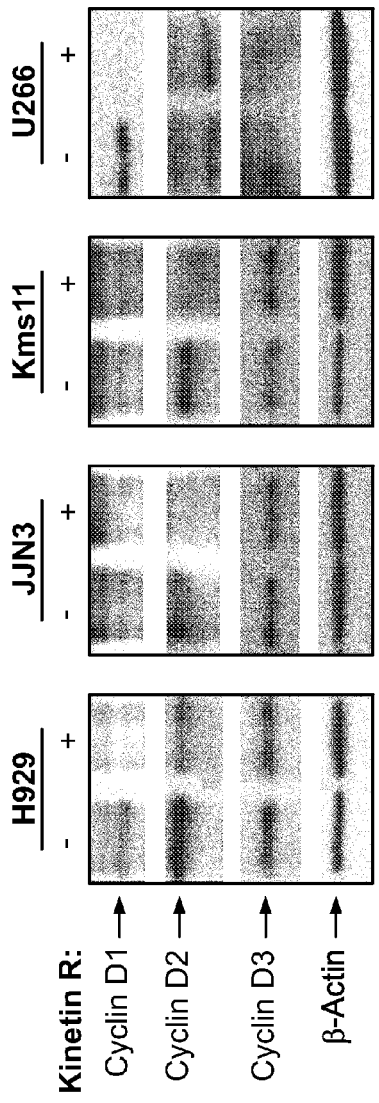
FIG. 2. Suppression of cyclin D2+cyclin D1 by kinetin riboside. Western blots showing suppressive effects of kinetin riboside 10 μM at 16 hours on cyclin D1 and D2 protein levels in (A) human myeloma cell lines (HMCL) and (B) primary patient CD138+ purified myeloma cells. Cyclin D1 and D2 in purified myeloma cells from patient E with multi-drug resistant plasma cell leukemia were unresponsive to kinetin riboside. Cyclin D3 levels in all HMCL and primary myeloma cells were unaffected. Caspase 9 cleavage was induced by kinetin riboside treatment in primary myeloma cells (B) (and in HMCL—see FIG. 5B). (C) Time course of cyclin D1 and D2 levels in the myeloma cell line H929 following kinetin riboside 10 μM exposure. (D) Dose titration of kinetin riboside on cyclin D2 levels in the HMCL, Kms11. As in part (A), kinetin riboside down-regulates cyclin D2 but not cyclin D1 in Kms11 cells.

This document provides methods and materials related to inhibiting cyclin D polypeptide activity. For example, this document provides methods and materials for using monensin, patulin, β-lapachone, camptothecin, dihydrogambogic acid, gentian violet, thapsigargin, brefeldin A, pristimerin, kinetin riboside, or combinations thereof to inhibit cyclin D polypeptide activity. In some cases, monensin, patulin, β-lapachone, camptothecin, dihydrogambogic acid, gentian violet, thapsigargin, brefeldin A, pristimerin, kinetin riboside, or combinations thereof can be used to treat cancer (e.g., a lymphoproliferative disorder such as multiple myeloma, Non Hodgkins Lymphoma, or other malignancy such as breast cancer or other cancer susceptible to cyclin D inhibition) or any neoplastic disorder in a mammal (e.g., a human). The methods and materials provided herein can be used to treat mammals having cancer cells (e.g., mammals having a myeloma cancer, Non Hodgkin lymphoma, breast cancer, or other cancer susceptible to cyclin D inhibition) such that the number of cancer cells is reduced (e.g., a 10, 20, 30, 40, 50, 60, 70, 80, 90, or 100 percent reduction). In some cases, an agent provided herein can be administered to a mammal having cancer cells such that the agent reduces cyclin D polypeptide activity within the mammal's cancer cells. Such a reduction in cyclin D polypeptide activity can result from the inhibition of the expression of nucleic acid encoding a cyclin D polypeptide within a mammal. For example, kinetin riboside can be used to reduce the level of cyclin D polypeptide activity in myeloma cancer cells within a mammal.

Typically, one or more of the agents provided herein (e.g., monensin, patulin, β-lapachone, camptothecin, dihydrogambogic acid, gentian violet, thapsigargin, brefeldin A, pristimerin, and kinetin riboside), either alone or in combination with an apoptotic agent, can be formulated into a pharmaceutical composition that can be administered to a mammal (e.g., rat, mouse, rabbit, pig, cow, monkey, or human) to treat cancer (e.g., myeloma). For example, kinetin riboside can be in a pharmaceutically acceptable carrier or diluent. A "pharmaceutically acceptable carrier" refers to any pharmaceutically acceptable solvent, suspending agent, or other pharmacologically inert vehicle. Pharmaceutically acceptable carriers can be liquid or solid, and can be selected with the planned manner of administration in mind so as to provide for the desired bulk, consistency, and other pertinent transport and chemical properties. Typical pharmaceutically acceptable carriers include, without limitation: water; saline solution; dimethyl sulfoxide; binding agents (e.g., polyvinylpyrrolidone or hydroxypropyl methylcellulose); fillers (e.g., lactose and other sugars, gelatin, or calcium sulfate); lubricants (e.g., starch, polyethylene glycol, or sodium acetate); disintegrates (e.g., starch or sodium starch glycolate); and wetting agents (e.g., sodium lauryl sulfate).

Monensin, patulin, β-lapachone, camptothecin, dihydrogambogic acid, gentian violet, thapsigargin, brefeldin A, pristimerin, and kinetin riboside can be synthesized, isolated from other materials, or purchased commercially. For example, monensin, patulin, β-lapachone, camptothecin, thapsigargin, brefeldin A, and kinetin riboside can be purchased from Sigma-Aldrich (St. Louis, Mo.). Dihydrogambogic acid and pristimerin can be purchased from Gaia Chemical Corporation (Gaylordsville, Conn.). In addition, compositions containing one or more of the agents provided herein can be admixed, encapsulated, conjugated, or otherwise associated with other molecules, molecular structures, or mixtures that can, for example, assist in uptake, distribution, and/or absorption. In some cases, an agent provided herein can be designed to be in the form of a salt or an ester. In some cases, an agent provided herein can be designed to contain one or more alkyl groups, alcohol groups, halogens, metals, or combinations thereof. For example, pristimerin or hydroxypristimerin (IUPAC Name: methyl 3,10-dihydroxy-2,4a,6a,6a,9,14a-hexamethyl-11-oxo-1,3,4,5,6,13,14,14b-octahydropicene-2-carboxylate) can be used as described herein.

The agents and compositions provided herein can be administered by a number of methods depending upon whether local or systemic treatment is desired and upon the area to be treated. Administration can be, for example, topical (e.g., transdermal, ophthalmic, or intranasal); pulmonary (e.g., by inhalation or insufflation of powders or aerosols); oral; or parenteral (e.g., by subcutaneous, intrathecal, intraventricular, intramuscular, or intraperitoneal injection, or by intravenous drip). Administration can be rapid (e.g., by injection) or can occur over a period of time (e.g., by slow infusion or administration of slow release formulations). For treating tissues in the central nervous system, the composition can be administered by injection or infusion into the cerebrospinal fluid, preferably with one or more agents capable of promoting penetration across the blood-brain barrier.

Compositions for topical administration include, for example, sterile and non-sterile aqueous solutions, non-aqueous solutions in common solvents such as alcohols, or solutions in liquid or solid oil bases. Such solutions also can contain buffers, diluents, and other suitable additives. Compositions for topical administration can formulated in the form of transdermal patches, ointments, lotions, creams, gels, drops, suppositories, sprays, liquids, and powders. Conventional pharmaceutical carriers, aqueous, powder or oily bases, thickeners, and the like can be added.

Compositions for oral administration include, for example, powders or granules, suspensions or solutions in water or non-aqueous media, capsules, sachets, or tablets. Such compositions also can incorporate thickeners, flavoring agents, diluents, emulsifiers, dispersing aids, or binders. Compositions for parenteral, intrathecal, or intraventricular administration can include, for example, sterile aqueous solutions, which also can contain buffers, diluents, and other suitable additives (e.g., penetration enhancers, carrier compounds, and other pharmaceutically acceptable carriers).

In some embodiments, a composition containing one or more of the agents provided herein can contain other therapeutic agents such as anti-inflammatory drugs (e.g., nonsteroidal anti-inflammatory drugs and corticosteroids).

Dosing is generally dependent on the severity and responsiveness of the cancer or disease state to be treated, with the course of treatment lasting from several days to several months, or until a cure is effected or a diminution of the disease state is achieved. Routine methods can be used to determine optimum dosages, dosing methodologies, and repetition rates. Optimum dosages can vary depending on the relative potency of individual agents, and can generally be estimated based on amounts found to be effective in in vitro and/or in vivo animal models. Typically, dosage is from about 0.01 μg to about 100 g per kg of body weight, and can be given once or more daily, weekly, or even less often. Following successful treatment, it may be desirable to have the patient undergo maintenance therapy to prevent the recurrence of the cancer or disease state.

The invention will be further described in the following examples, which do not limit the scope of the invention described in the claims.

EXAMPLES

Example 1

Chemical Library Screening Identifies Inhibitors of Cyclin D2 (CCND2) Transactivation that Selectively Induce Apoptosis in Multiple Myeloma Cells Non malignant proliferating human tissues typically co-express three cyclin D polypeptides (D1, D2 and D3) that are essentially interchangeable due to substantive functional redundancy. In contrast, many cancers achieve sustained cell cycle deregulation by over-expressing a single cyclin D. Such tumors therefore differ from normal proliferating tissues in their dependence upon a single cyclin D for excess growth. Selective suppression of the cyclin D gene exploited by such tumors may be an effective and universal targeted therapeutic strategy.

Multiple myeloma tumors universally target one of the three human cyclin D genes (CCND1, CCND2 or CCND3) for dysregulation (Bergsagel et al., 2005, *Blood*, 106:296). As myeloma tumors universally dysregulate a cyclin D gene, commonly CCND1 or CCND2, it was tested whether silencing of one or both of these genes could induce growth arrest or cytotoxicity in myeloma cells, and thus whether targeting of specific cyclin Ds could represent a valid therapeutic approach in this malignancy. H929 myeloma cells were infected with lentivirus (LV) vectors expressing shRNA targeting either cyclin D1 or cyclin D2, or with control LV expressing non-targeting (NT) shRNA, and the effects on cellular proliferation and viability were determined. Using conditions that resulted in >99% cellular infection and effective cyclin D gene silencing, substantial $G_0/G_1$ cell cycle arrest with silencing of either cyclin D1 or cyclin D2 was observed, but not with control NT LV, confirming the importance of cyclin D dysregulation to H929 cells. Suppression of both cyclin D1 and D2 caused a 64% reduction in S-phase progression. Silencing of cyclin D1 and or D2 was also associated with delayed myeloma cell apoptosis that was prominent by day 7 post infection. Combined cell cycle arrest and apoptosis together resulted in substantial reductions in viable H929 numbers. Knockout mouse models indicate that most somatic tissues can develop in the complete absence of any D-cyclin (Kozar et al., 2004, *Cell*, 118:477). Taken together, these results indicate that specific silencing of cyclin D2 or D1 can be employed to achieve a targeted anti-myeloma therapeutic effect.

To identify pharmaceutical inhibitors of CCND2 transactivation, an assay employing NIH 3T3 cells stably co-expressing the CCND2 transactivator c-Maf and the cyclin D2 promoter driving firefly luciferase (luc) was developed. Using this assay, Lopac (n=1280), Prestwick (n=1120), and Spectrum (n=2000) libraries of drugs and natural compounds were screened. In a parallel MTS assay, the effect of each compound on 3T3 viability was determined, allowing exclusion of compounds that caused secondary suppression of CCND2 due to non-specific cytotoxicity. From the screen, 10 c-Maf independent putative CCND2 inhibitors were identified. These included monensin, patulin, β-lapachone, camptothecin, dihydrogambogic acid, gentian violet, thapsigargin, brefeldin A, pristimerin, and kinetin riboside. Three of the 10 compounds (gentian violet, thapsigargin and patulin) may exhibit toxicity as determined from the literature.

Subsequent validation studies using selected compounds in human myeloma cell lines (HMCL) confirmed successful suppression of both cyclin D2 and D1 polypeptides. Each of these compounds was then shown to be cytotoxic to a genetically diverse and standardized panel of 14 HMCL in MTT assays: monensin (10-760 nM), camptothecin (5-700 nM), dihydrogambogic acid (250-800 nM), pristimerin (150-500 nM), and kinetin riboside (2.5-20 μM). Cell cycle analysis confirmed induction of $G_0/G_1$ phase arrest for most compounds, consistent with cyclin D inhibition. However, camptothecin and β-lapachone induced S-phase arrest, suggesting secondary suppression of cyclin D by virtue of S-phase activity.

Unsorted myeloma patient bone marrow samples demonstrated selective activity for pristimerin, dihydrogambogic acid, and kinetin riboside against $CD138^+$ myeloma cells compared with non malignant hematopoietic cells. By contrast, monensin exhibited almost equal toxicity for normal cells. The triterpenoid, pristimerin, exhibited potent anti-myeloma activity and was examined in greater detail. Studies confirmed that pristimerin rapidly inhibits cyclin D1, D2, and D3 expression (<6 hours) at nanomolar concentrations and induces apoptosis of primary myeloma cells characterized by caspase 9 cleavage and Annexin V binding. While pristimerin is cytotoxic to HMCL and patient myeloma cells at 0.1-0.15 mg/L, toxicity studies in vivo indicate that the drug is tolerated in mice at 2.5 mg/kg i.p. daily. In vivo anti-myeloma activity against a xenograft model can be confirmed using monensin, patulin, β-lapachone, camptothecin, dihydrogambogic acid, gentian violet, thapsigargin, brefeldin A, pristimerin, and kinetin riboside.

Example 2

Kinetin Riboside, a Targeted Inhibitor of CCND1 and CCND2, Exhibits Anti-Myeloma Activity Methods and Materials Cell culture, genetic constructs and transduction. Mouse fibroblast NIH3T3 cells were maintained in Dulbeco's Modified Eagle's Medium. Human myeloma cell lines (HMCL) and primary patient cells were maintained in Iscove modified Dulbecco medium (IMDM). All cultures were supplemented with 10% fetal bovine serum (FBS), 1 mM glutamate and antibiotics. Patient cells were additionally supplemented with interleukin 6 (IL-6). Cells were cultured at 37° C. in humidified 5% $CO_2$.

Full-length c-maf cDNA was subcloned into an IRES-GFP MIEV retroviral vector and introduced into NIH3T3 cells by infection. Stable clones expressing GFP and c-maf were selected by flow cytometry and immunoblotting, respectively. The promoter of human cyclin D2 (−894 to −4; Brooks et al., *J. Biol. Chem.*, 271, 9090-9 (1996)), containing c-maf responsive element sequence (MARE), was cloned from DNA from HeLa cells and inserted into the pGLbasic firefly luciferase vector (Promega, Madison, Wis.) immediately upstream of the luciferase gene. This construct was co-transfected with pcDNA3 (containing a neomycin resistance gene) into both NIH3T3 wild type cells and NIH3T3 cells stably over-expressing c-maf-IRES-GFP. Cells stably expressing c-maf, GFP, and luciferase were selected.

High throughput screen for inhibitors of CCND2 transactivation. NIH3T3 cells stably expressing c-maf and the CCND2 promoter driving luciferase (13,000 cells per well) were plated in 96-well plates by a Biomek FX liquid handler (Beckman, Fullerton, Calif.). After the cells had adhered, they were treated with aliquots of molecules from LOPAC (Sigma, St. Louis, Mo.), Prestwick (Prestwick Chemical Inc, Illkirch, France) or Spectrum (Microsource Discovery Systems, Gaylordsville, Conn.) libraries of off-patent drugs and chemicals at a final concentration of ~5 µM and <0.1% DMSO. Cells were incubated with compounds at 37° C. for 16 hours. After incubation, CCND2 transactivation was assessed by the luciferase assay, and viability was assessed by MTS assay.

Luciferase assay. Luciferase activity was assessed according to the manufacturer's instructions (Promega, Madison, Wis.). Briefly, the cell culture medium was removed using an EMBLA plate washer (Molecular Devices, X) and Glo Lysis buffer (Promega) was added by robot. After a 10-minute incubation, an equal volume of Bright-Glo Luciferase substrate (Promega) was added, and luminescence signal was detected with a 96-well Luminoskan luminescence plate reader (Thermo Labsystem, Waltham, Mass.) using a 5 second integration.

Viability assay. The effects of screened compounds on cell viability was assessed by 3-(4,5-dimethyl-2-yl)-5-(3-carboxymethoxyphenyl)-2-(4-sulfophenyl)-2-H-tetrazolium (MTS) assay according to the manufacture's instructions (Progmega, Madison, Wis.). MTS reagent (20 µL/well in 96 well plates) was added to cells, and these were then incubated at 37° C. for 4 hours. Absorbance at 490 nm was determined using a 96-well plate reader.

Studies of kinetin riboside using 3T3-D2-luc cells. To examine CCND2 suppression induced by kinetin riboside, the reporter cells were exposed to kinetin riboside in combination with other drugs (all purchased from Sigma, St. Loius, Mo.) that influence CCND2 transcription or inhibit nucleoside transport or phosphorylation. NIH3T3 cells expressing the CCND2 promoter driving luciferase were incubated with kinetin riboside or vehicle control +/− forskolin, 4-(3-butoxy-4-methoxybenzyl)imidazolidin-2-one (BMBI), cantharadin, S-(4-Nitrobenzyl)-6-thioinosine (NBTI), or A-134974, as specified at 5 µM concentration for 16 hours at 37° C. CCND2 transactivation and viability were subsequently assessed by the method described for drug library screening with the exception that assays were performed manually. Forskolin is a cell-permeable diterpenoid that activates adenylate cyclase resulting in increased cAMP concentration. BMBI (Sigma B8279) is an inhibitor of cAMP phosphodiesterase that also causes accumulation of cAMP. Cantharadin (C7632) is an inhibitor of protein phosphatase 2A and, from the library screen, mediates induction of CCND2. NBTI (Sigma N2255) is a potent adenosine uptake inhibitor, and A-134974 (Sigma A2846) is a selective inhibitor of adenosine kinase.

Primary $CD138^+$ myeloma cell purification. Samples from patients diagnosed by International Myeloma Working Group criteria were included in this study. Bone marrow processing, including red cell lysis using ammonium chloride and $CD138^+$ plasma cell purification, was performed as described elsewhere (Abraham et al., *Blood,* 105, 794-803 (2005)). Research BM samples were obtained following informed consent at the time of routine procurement of clinical samples.

Immunoblotting. Cytosolic extracts were prepared from HMCL or purified patient $CD138^+$ myeloma cells following exposure to kinetin riboside. Cells were washed with cold PBS, resuspended in cold RIPA buffer ($5 \times 10^6$ cells/100 µL) containing fresh protease and phosphatase inhibitors (Santa Cruz Biotechnology, Santa Cruz, Calif.) and incubated on ice for 30 minutes with gentle mixing. The supernatant was repossessed following high speed centrifugation, and protein concentrations were determined by the Bradford assay. Immunoblot assays were performed as described elsewhere (Krajewski et al., *Anal. Biochem.,* 236:221-228 (1996)). Briefly, equal amounts of protein were separated by SDS-PAGE and transferred to a PVDF nitrocellulose membrane using a semi-dry apparatus. Membranes were blocked using 5% skim milk in Tris buffered saline and probed with monoclonal mouse anti-cyclin D1 (DCS-6, Biosource, Camarillo, Calif.), polyclonal rabbit anti-cyclin D2 (#2924, Cell Signalling Technology), monoclonal mouse anti-cyclin D3 (DCS-22, BioSource), polyclonal rabbit anti-c-Maf (M-153, Santa Cruz), polyclonal rabbit anti-Cleaved Caspase 9 (Asp315) (Cell Signaling Technology), monoclonal mouse anti-β-actin (Cell Signaling Technology) and/or monoclonal anti-a-tubulin (B-7)(Santa Cruz Biotechnology, Santa Cruz, Calif.). Membrane proteins were visualized using HRP-conjugated species-specific secondary antibodies (Cell Signaling Technology) and enhanced chemiluminescence (Pierce, Rockford, Ill.).

Flow cytometry. HMCL were treated as indicated and then washed in cold phosphate-buffered saline (PBS) and resuspended in buffer containing AnnexinV-FITC and propidium iodide (BD Biosciences, San Jose, Calif.) for 15 minutes at room temperature. Cells ($10^5$) were subsequently diluted and analyzed immediately by flow cytometry (FACScan, BD Biosciences, San Jose, Calif.) using CellQuest software. Patient bone marrow specimens were prepared and analyzed in a similar fashion using AnnexinV-FITC and anti-CD138-PE (BD Biosciences, San Jose, Calif.).

Cell cycle profiling. HMCL were incubated with drug or vehicle as indicated, washed and resuspended in 1 mL PBS. Ice cold ethanol was added dropwise to 75% with regular mixing, and suspensions were incubated at −20° C. for 1 hour. Cells were washed again with PBS and resuspended in 0.1 mL RNAse A (100 µg/mL) at room temperature for 5-10 minutes. Propidium iodide (200 µL×100 µg/mL) was added immediately prior to analysis by flow cytometry. Cellular aggregates were excluded using CellQuest Doublet Discriminator Module, and cell cycle profile was determined using ModFit LT Mac 3.1 SP2 (Verity Software House, TopSham, Me.).

Gene expression profiling. H929 and U266 HMCL were treated with kinetin riboside (5 µM), an unrelated cytotoxic pristimerin (0.5 µM), or DMSO vehicle for 4 hours under normal culture conditions. RNA was then isolated using Trizol and further purified by Qiagen column, according to the manufacturer's instructions and was assessed using a Bio- Analyzer 2100 (Agilent Technologies, Palo Alto, Calif.). Microarray hybridization using Affymetrix Hg_U133_2+ chips (Affymetrix, Santa Clara, Calif.) was performed as described elsewhere (Abraham et al., Blood 105, 794-803 (2005)). Gene expression intensity values were log transformed, normalized by chip and by cell line to DMSO-control treated samples and analyzed using GeneSpring 7 (Agilent Technologies, Palo Alto, Calif.). Expression values were filtered by raw intensity level to exclude non-expressed probe-sets with raw expression within one log (10) of the minimum level observed. Only probe sets with sub-threshold intensities in all samples (treated and untreated) were excluded.

Analysis of CREM gene variant transcript expression. Affymetrix probe-sets targeting CREM gene expression were correlated with activator and repressor variant transcripts using Ensembl (Birney et al., Nucleic Acids Res., 34, D556-61 (2006)) Human ContigView v39 (www.ensembl.org/Homo sapiens) and NCBI plus Vega (Ashurst et al., Nucleic Acids Res., 33, D459-65 (2005)) mRNA transcript databases.

Results

High throughput assay for inhibitors of transactivation of CCND2. Inhibitors of CCND2 transactivation were identified and characterized for c-maf dependence or independence. To identify inhibitors, a high-throughput chemical genetics screen using NIH3T3 cells stably over-expressing the cyclin D2 promoter driving firefly luciferase (luc) with or without co-expression of a c-Maf was developed. NIH3T3 fibroblasts were chosen for the initial screening assay as fibroblasts survive and proliferate in the absence of D cyclins. Consequently, using fibroblasts allowed for the ability to distinguish between drugs that caused specific suppression of CCND2 without affecting 3T3 cell viability and drugs that caused suppression of CCND2 or luciferase associated with non-specific cytotoxicity.

In an optimized automated assay, NIH3T3 cells over-expressing c-maf and the human cyclin D2 promoter driving luc were plated in 96-well plates by robot and following adhesion were treated for 16 hours with compounds at a final concentration of ~5 µM and <0.1% DMSO. As a control, cells were treated with buffer alone. Following incubation at 37° C., CCND2 transactivation was assessed by luciferase assay, and cellular viability was assessed by MTS assay. Thus, each compound from the library was tested in at least two assays—luciferase for CCND2 activity and MTS for viability. The coefficient of variance (CV) of the assay was <10%.

More than 4000 drugs and natural compounds from Lopac (n=1280), Prestwick (n=1120), and Spectrum (n=2000) libraries were screened to identify inhibitors of CCND2 transactivation. Putative 'hits' were identified as compounds that preferentially reduced luciferase activity disproportionately to any change in 3T3 viability and were empirically defined as compounds that induced 50% or more reduction in luciferase expression relative to cell viability.

The majority of hits from the Lopac and Prestwick libraries were glucocorticosteroid family members. These decrease cyclin D expression via c-Maf dependent and independent mechanisms. Similarly, from the Spectrum library screen (FIG. 1a) 38 hits were identified, of which 29 were recurrent glucocorticoid hits identified originally during screening of the Lopac and Prestwick libraries. However, in addition a further nine non-steroid compounds were identified as putative suppressors of CCND2 and these included: kinetin riboside, dihydrogambogic acid, monensin, patulin, gentian violet, pararosaniline pamoate, pristimerin, aklavine, and camptothecin.

Exclusion of non-specific or toxic assay 'hits.' Drugs that decreased luciferase activity without affecting viability may cause reduced transactivation of the cyclin D2 promoter, or may act non-specifically on the activity of the luciferase enzyme. To distinguish between these two possibilities, hits were re-tested against NIH3T3 cells that over-expressed luciferase driven by an RSV promoter. From this testing, patulin was found to non-specifically reduce luciferase activity and on repeat testing both patulin and aklavine caused excess NIH3T3 cytotoxicity. Therefore, these drugs were excluded from further analysis. However, other spectrum hits did not decrease luciferase activity when this was driven by the RSV promoter and therefore act specifically via the CCND2 promoter.

Figure 12A:
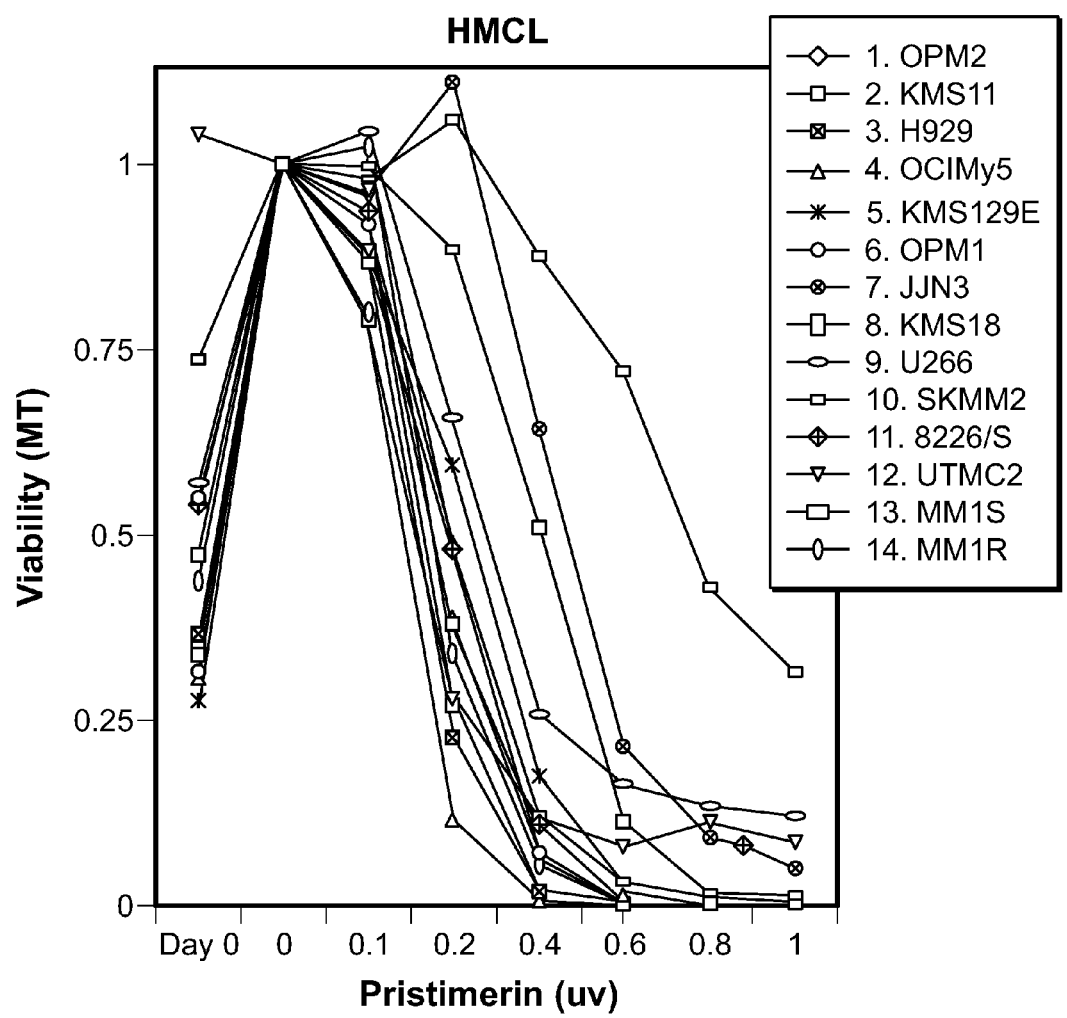
FIG. 12. (A) Pristimerin is cytotoxic to HMCL and shows specific cytotoxicity to patient primary myeloma tumor cells with limited toxicity to normal bone marrow progenitors. HMCL viability after exposure to pristimerin at concentrations of 0.1-1.0 µM; assessed by MTS assay at 48 hours. (B) Flow cytometry of two representative myeloma patient bone marrow samples, i-ii, showing relative cytotoxicity of pristimerin to primary CD138$^+$ myeloma cells versus CD138$^-$ hematopoietic cells at 48 hours. Following treatment, most CD138$^+$ cells become apoptotic (Annexin V-positive and CD138-negative) while only modest toxicity is observed in the CD138⁻ bone marrow progenitor compartment.
Figures 1, 12B:
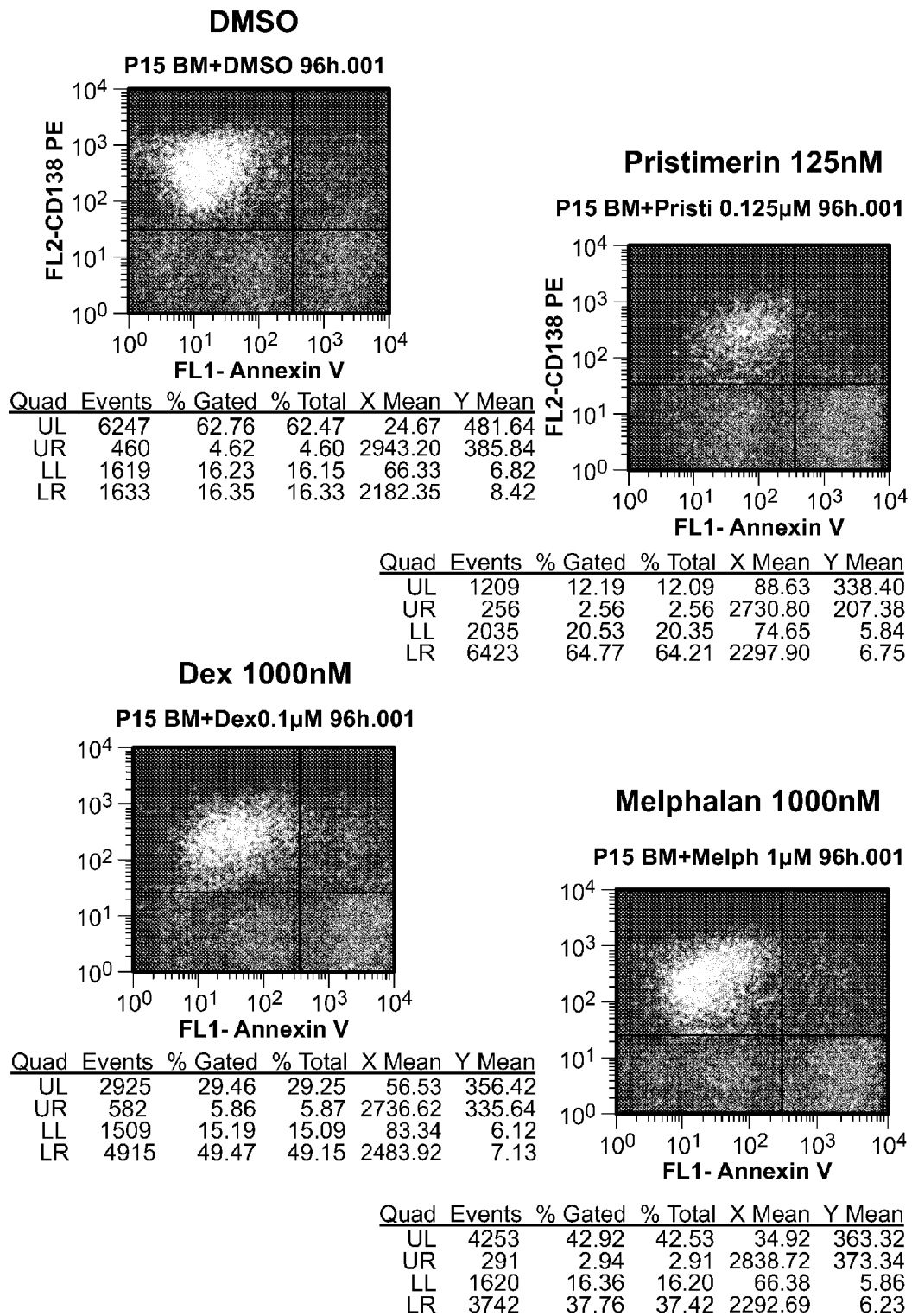
FIG. 1. Screening of the Spectrum library for inhibitors of CCND2 transactivation. (A) Dot plot of the Spectrum library of 2000 drugs and natural compounds and their effects on CCND2 promoter transactivation (measured by luciferase assay) relative to NIH3T3 viability (MTS). The Lopac and Prestwick drug libraries were also screened but are not shown. (B) Secondary and tertiary screening of short-listed Spectrum library hits showing the influence of these drugs on normalized luciferase expression when expressed under the control of a control RSV promoter or the CCND2 promoter (in the absence or presence of c-Maf). Kinetin riboside, DHGA, and pristimerin each show reproducible c-maf independent specific suppression of the CCND2 promoter; the drugs do not non-specifically suppress luciferase protein function. The influence of hits on CCND2-promoter driven luciferase in the presence of c-maf overexpression is also shown. (C) Time course of kinetin riboside-mediated suppression of CCND2-driven luciferase in NIH3T3. (D) Chemical structure of kinetin riboside.
Figure 12B:
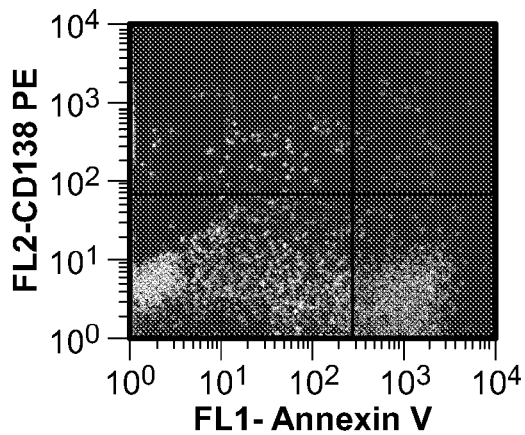

To focus subsequent efforts, compounds reported to have toxicities likely to prevent in vivo or clinical systemic use were excluded, including pararosaniline pamoate and gentian violet (NTP Toxicology and Carcinogenesis Studies of C.I. Basic Red 9 Monohydrochloride (Pararosaniline) (CAS No. 569-61-9) In F344/N Rats and B6C3F1 Mice (Feed Studies). Natl Toxicol Program Tech Rep Ser 285, 1-228 (1986); Docampo & Moreno, Drug Metab Rev 22, 161-78 (1990); Au et al., Mutat Res 66, 103-12 (1979); and Parker & Binder, Am J Ophthalmol 87, 340-3 (1979)). Monensin was also excluded following preliminary validation experiments as it exhibited excessive non-specific toxicity towards non-malignant patient hematopoietic cells. Finally, camptothecin was excluded as this drug can interfere with DNA synthesis and likely only indirectly influences cyclin D levels by virtue of its S-phase activity (Del Bino & Darzynkiewicz, Cancer Res., 51, 1165-9 (1991); Hennequin et al., Cancer Res., 54, 1720-8 (1994); Shao et al., Cancer Res., 57, 4029-35 (1997); and Coley et al., Anticancer Drug Des., 7, 471-81 (1992)).

c-Maf-dependent versus-independent inhibitors of cyclin D2. Hits that decreased CCND2 transactivation in the assay may act through c-maf dependent or independent mechanisms. To distinguish between these possibilities, the remaining hits were assessed for their activity on NIH 3T3 cells containing the CCND2-luc reporter gene with or without co-expression of c-maf (untransformed 3T3 do not have detectable levels of c-maf by immunoblotting). The three non-steroid hits reduced CCND2 transactivation in cells both in the absence or presence of c-maf over-expression (FIG. 1b). Thus, these compounds function independently of cMaf to inhibit cyclin D2 transactivation.

Kinetin riboside is an inhibitor of CCND1+CCND2 transactivation and blocks myeloma cells from entering the cell cycle. Of the non-steroid putative inhibitors of CCND2, kinetin riboside, was studied in detail. Kinetin riboside (N6-Furfuryladenosine) is a synthetic cytokinin and nucleoside derivative (FIG. 1c) and reproducibly induces rapid suppression of CCND2 transactivation in 3T3 fibroblasts (FIG. 1d). Cytokinins are a family of natural plant hormones that promote resting plant cells to divide via transcriptional induction of cyclin D3 (Riou-Khamlichi et al., Science 283, 1541-4 (1999)). Kinetin riboside-induced suppression of CCND2 in the above assay suggested that this compound may have a parallel but antagonistic function on cyclin D transcription in mammalian cells. To further investigate kinetin riboside activity, the influence of this compound on cyclin D gene expression in a human malignancy model was validated.

Kinetin riboside was tested against a panel of human myeloma cell lines (HMCL). These cell lines have a range of transforming events relevant to myeloma including FGFR3/MMSET (H929, Kms11), c-Maf (BN3, Kms11) or CCND1 (U266) deregulation due to chromosomal translocations. As a consequence, these HMCL all over-express either cyclin D1 or D2. As shown in FIG. 2A, kinetin riboside caused significant suppression of cyclin D1 and/or D2 proteins in all HMCL tested, but did not influence cyclin D3 levels. Kinetin riboside induced suppression of cyclin D1 in the HMCL, U266, despite cis dysregulation of the CCND1 gene in this line by translocation to the IgH enhancer. By contrast the HMCL, Kms11, which is transformed both by FGFR3/MMSET and c-maf translocations targeting CCND2, and by c-Myc over-expression, exhibited significant suppression only of cyclin D2 but not D1, indicating discrete regulatory processes affecting these genes.

Figure 2B:
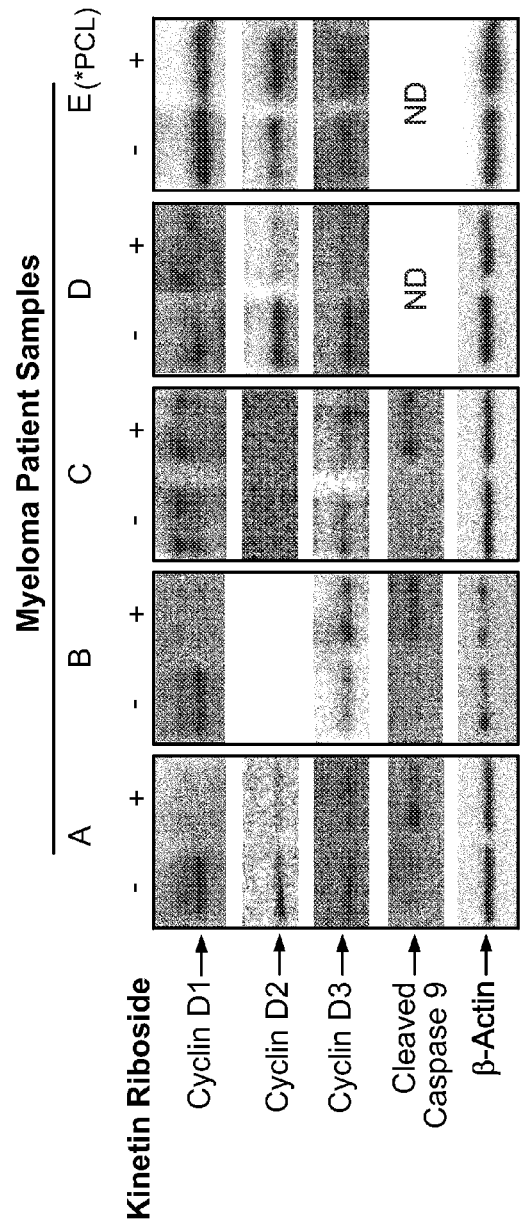

HMCL proliferate ex vivo and are not always representative of primary tumor samples. The effects of kinetin riboside on cyclin D expression in purified CD138+ cells from myeloma patient bone marrow aspirates were tested. Purified CD138+ myeloma cells from patient samples do not proliferate well in vitro, and cyclin D levels rapidly decline in culture. Nevertheless, in 4 of 5 samples (FIG. 2B), kinetin riboside induced suppression of cyclin D1 (samples A-C) or D2 (sample D) beyond any decline associated with in vitro culture. In a 5th case (sample E), cyclin D1 and D2 levels appeared preserved in purified CD 138+ patient cells after in vitro culture and were unaffected by kinetin riboside treatment. This sample was derived from a patient with plasma cell leukemia (PCL).

Figure 2C:
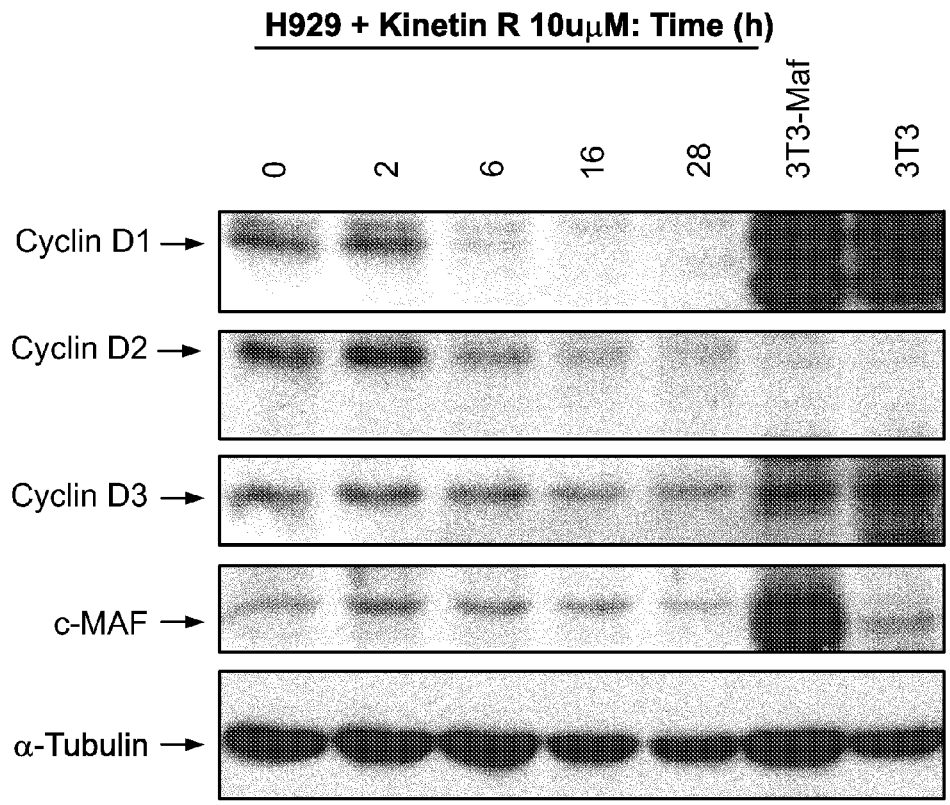
Figure 2D:
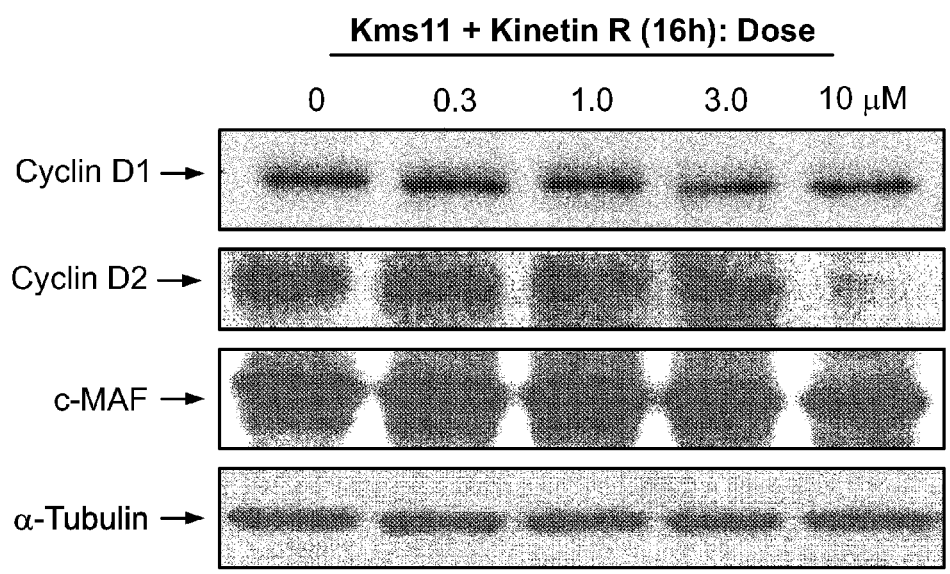
Figure 3A:
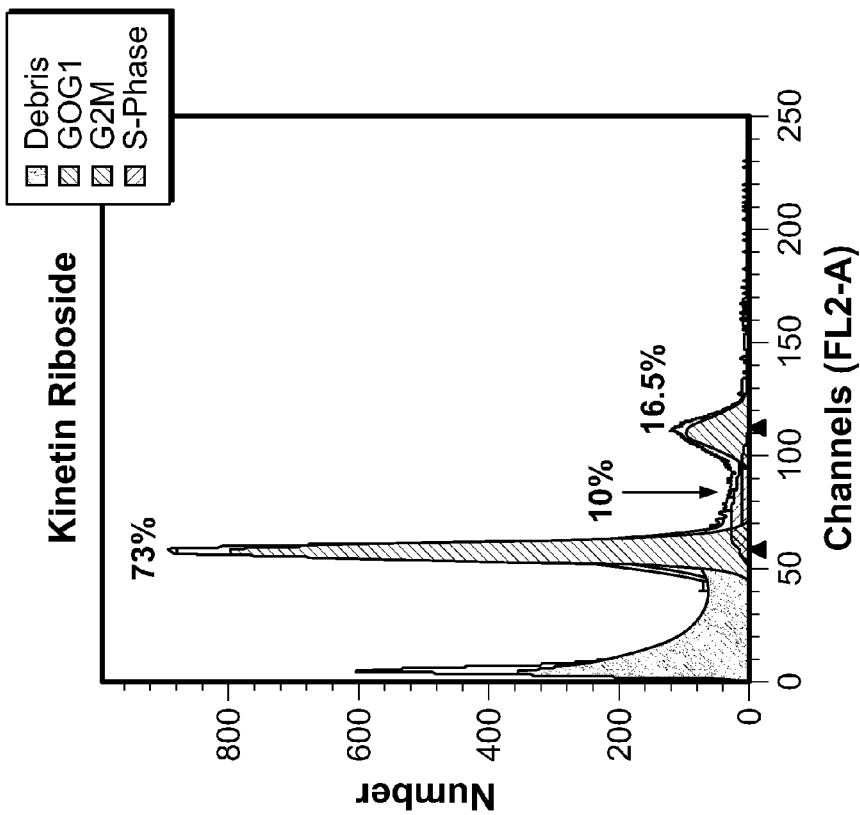
FIG. 3. Kinetin riboside causes cell cycle arrest at G0/G1 and prevents S-phase entry. Effect of DMSO vehicle or kinetin riboside 10 µM on the cell cycle profiles of (A) H929 and (B) U266 HMCL at 20 hours. Red peaks represent G0/G1 phase (left) 2N ploidy (both cell lines are hypodiploid) and G2/M phase (right) 4N ploidy; diagonal shading represents intermediate DNA content corresponding to S-phase.
Figure 3A:
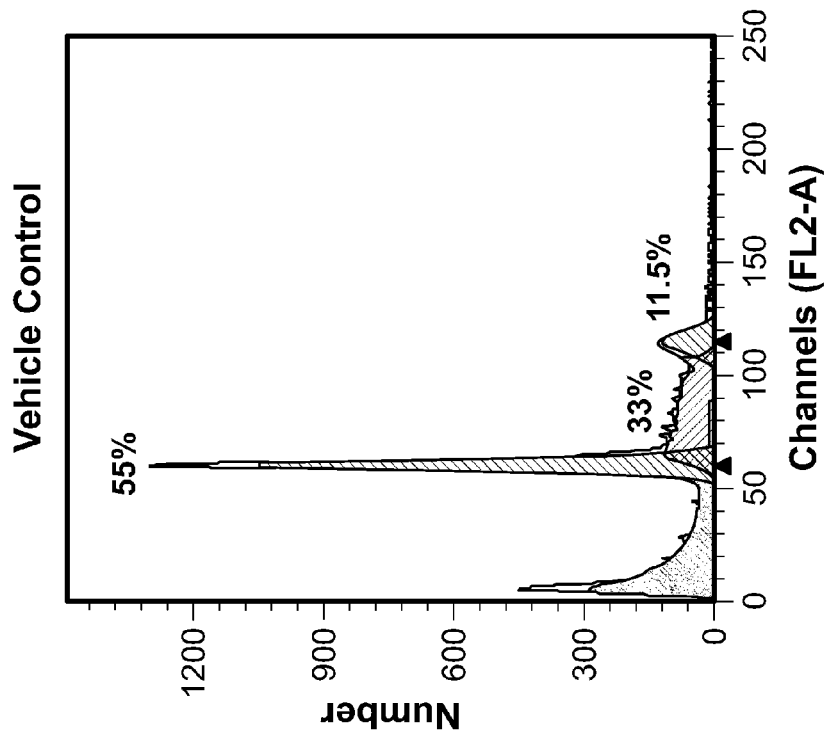
Figure 3B:
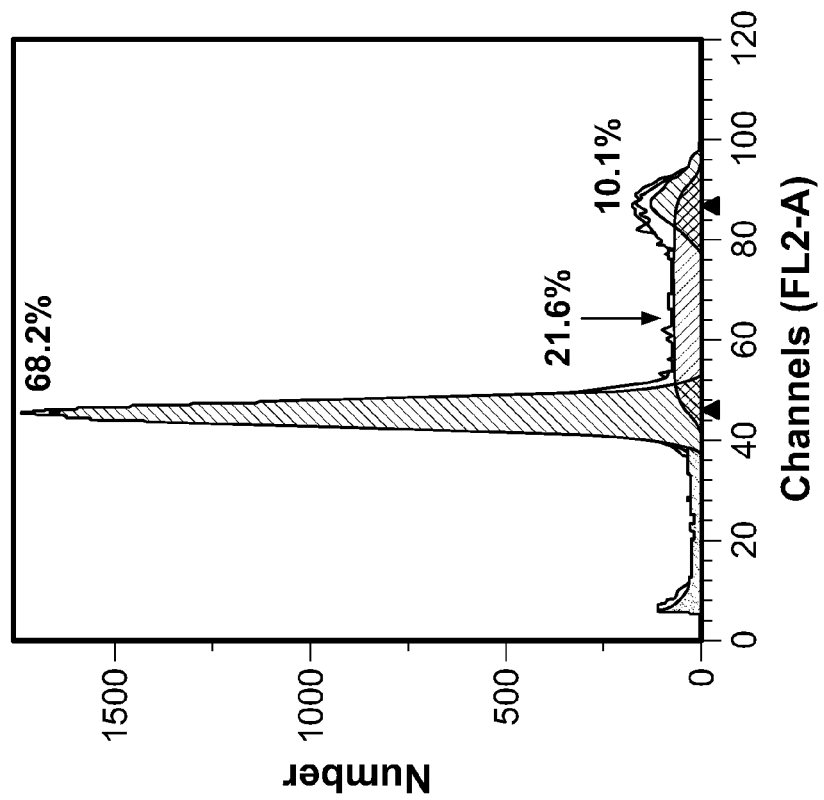
Figure 3B:
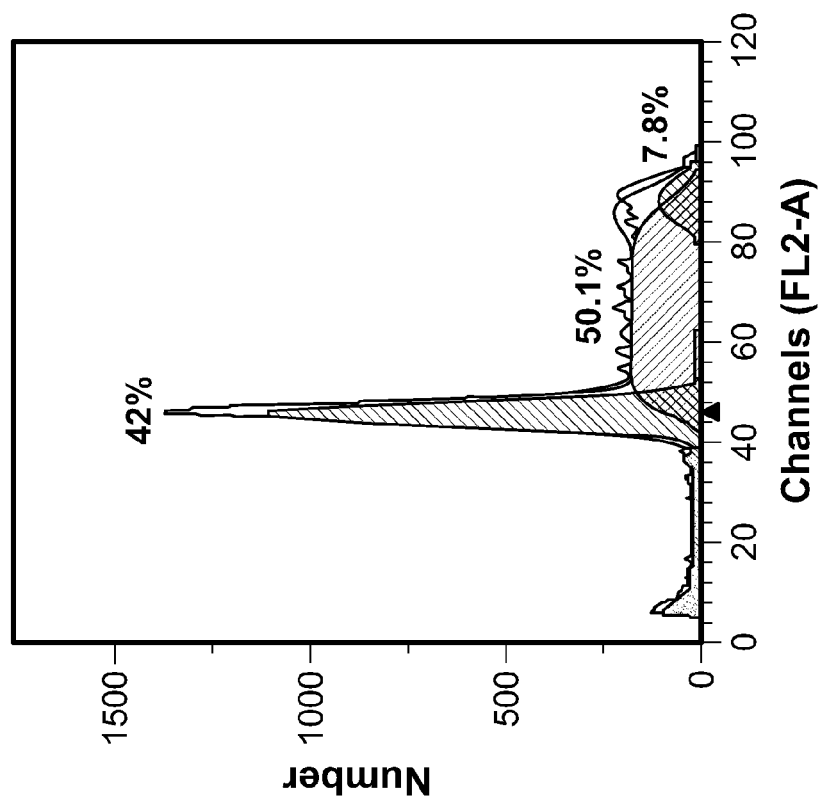
Figure 4A:
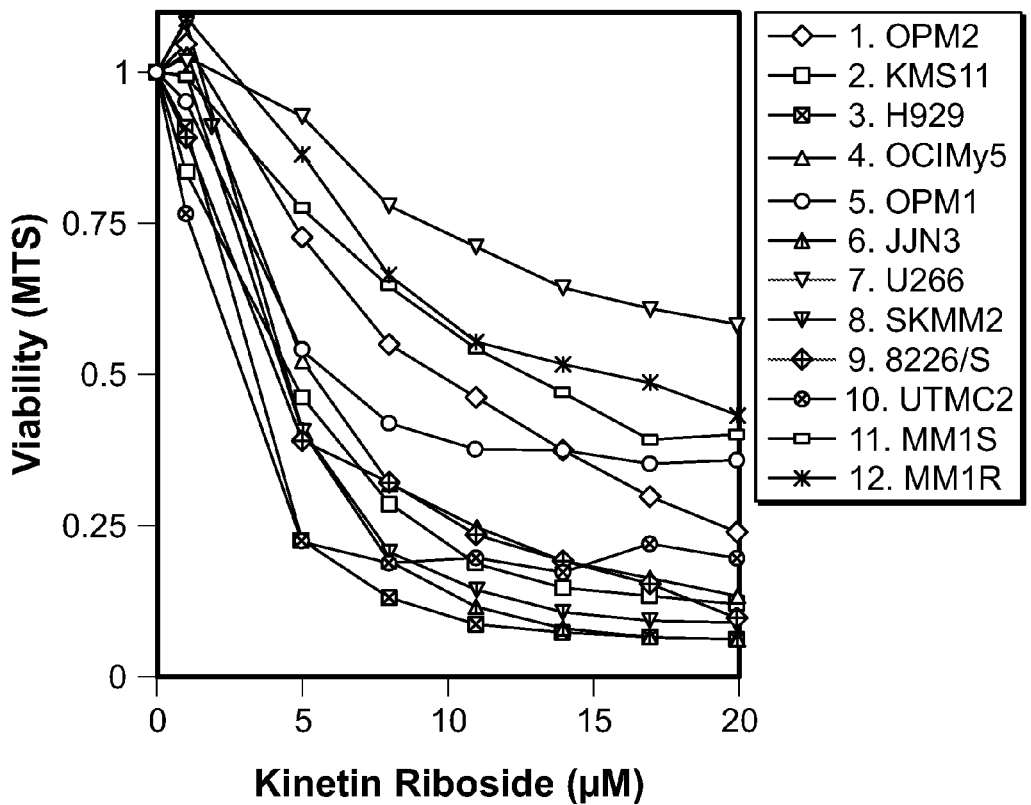
FIG. 4. Kinetin riboside induces growth arrest and apoptosis in HMCL and primary CD138+ myeloma cells and shows synergistic cytotoxicity with corticosteroids. (A) HMCL viability after exposure to kinetin riboside at concentrations 1-20 µM; assessed by MTS assay at 48 hours. (B) HMCL apoptosis assessed by Annexin V binding, versus loss of membrane integrity (propidium iodide uptake) at 96 hours. (C) Density of viable cells of HMCL in culture at 96 hours after treatment with kinetin riboside (10 µM) (total cell density×% [Annexin V negative]). Whereas H929 cells respond to kinetin riboside 10 µM by apoptosis (A), U266 respond predominantly by growth inhibition (B-C) associated with cell cycle arrest (FIG. 3). (D) Flow cytometry of a representative myeloma patient bone marrow sample showing relative cytotoxicity of kinetin riboside to primary CD138+ myeloma cells versus CD138− hematopoietic cells at 48 hours. Following treatment, most CD138+ cells become apoptotic (Annexin V-positive and CD138-negative) while only modest toxicity is observed in the CD138− bone marrow progenitor compartment. (E) Cytotoxic synergy of kinetin riboside (5 µM) and dexamethasone (10 nM) for JJN3, MM1.S and My5 HMCL; assessed by MTS assay at 48 hours.
Figure 4C:
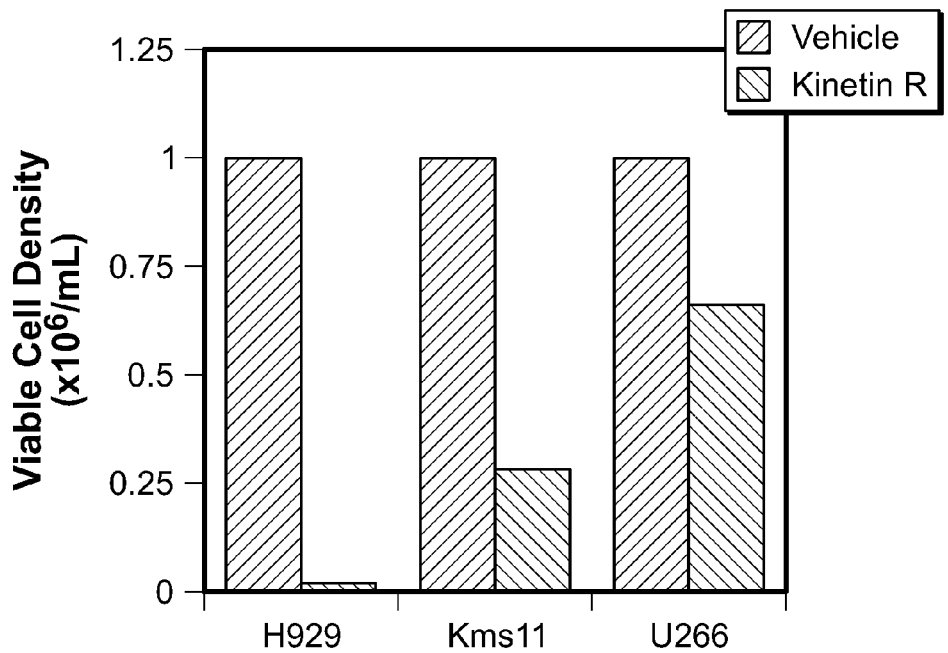

Kinetin riboside caused rapid suppression of cyclin D1 and D2 proteins within 6 hours (FIG. 2C). However, kinetin riboside did not significantly affect cyclin D3 levels until 28 hours or later, when a proportion of cells have already undergone apoptosis (see below and FIG. 4C).

Figure 2:
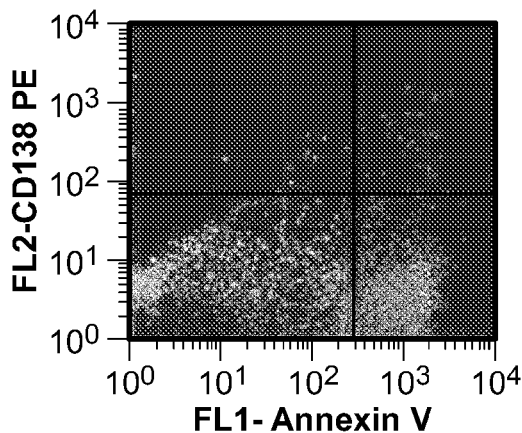
Figure 13A:
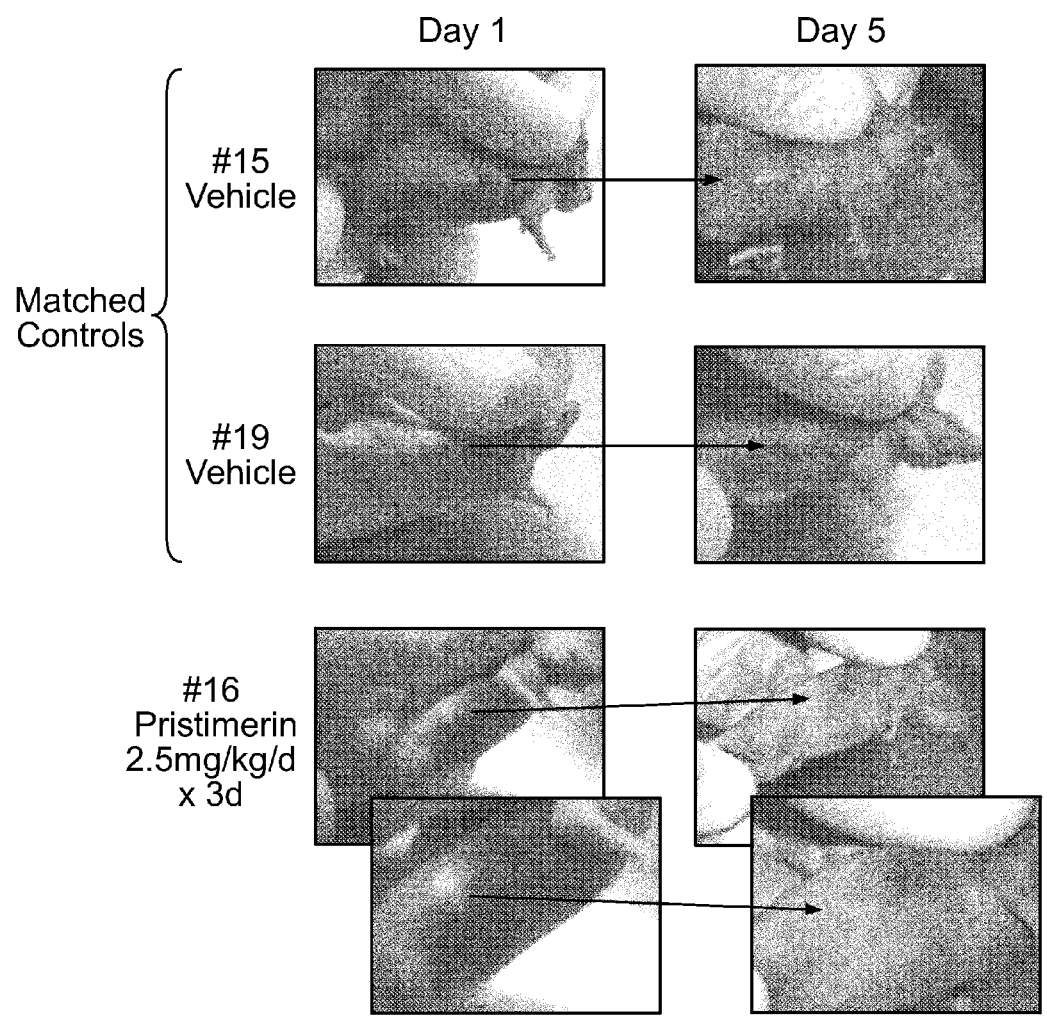
FIG. 13. Tumorical activity of Pristimerin in vivo. RPMI-8226 HMCL cells ($2 \times 10^7$) in 50% (v/v) Matrigel matrix were implanted subcutaneously in the right flank of BNX (Beige-Nude-X-linked immune deficient) mice and tumors were allowed to establish over 2 weeks until an average tumor volume of 150 mm$^3$ was obtained. Mice were then treated with vehicle control or pristimerin 2.5 mg/kg/day for 3 days and response was assessed on days 3 and 5. (A) Photographic record of response of a pristimerin-treated mouse versus matched controls treated with vehicle alone. (B) Mean tumor volume of controls versus pristimerin-treated mice.
Figure 13B:
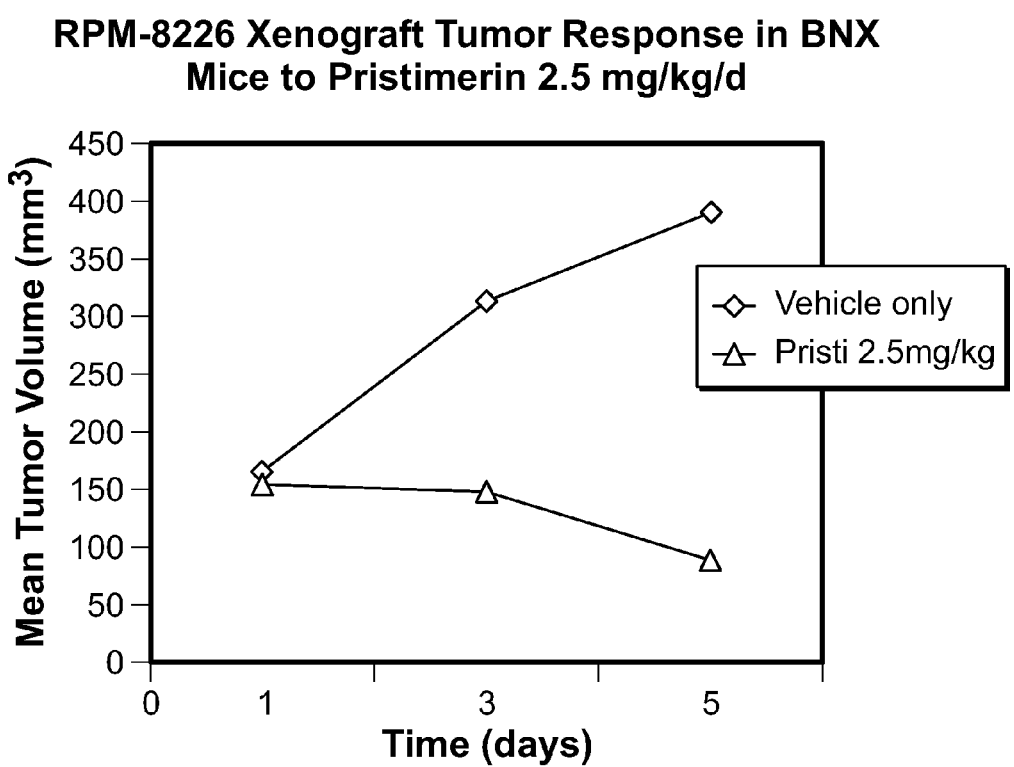

To verify that the rapid suppression of cyclin D1 and D2 induced by kinetin riboside treatment is a direct effect, and does not occur secondary to cellular arrest in S-phase (when CCND1 and CCND2 are normally suppressed), the influence of kinetin riboside on the cell cycle profile of cultured HMCL was examined (FIG. 3). Within 20 hours, kinetin riboside caused the proportion of cells entering S-phase to fall by 50-70% in all HMCL tested, with a corresponding increase in the G0/G1 fraction. This suggests that rather than causing indirect suppression of cyclin D genes by first arresting cells in S-phase, kinetin riboside acts directly to suppress cyclin D1 and D2 and as a consequence cells are prevented from entering the cell cycle or transiting beyond G1. Suppression of cyclin D1 and D2 by kinetin riboside is therefore observed (FIG. 2) despite increased numbers of cells in G0/G1-phase (FIG. 3) when high levels of cyclin D1 and/or D2 are typically expressed in continuously dividing cell lines.

Figure 4B:
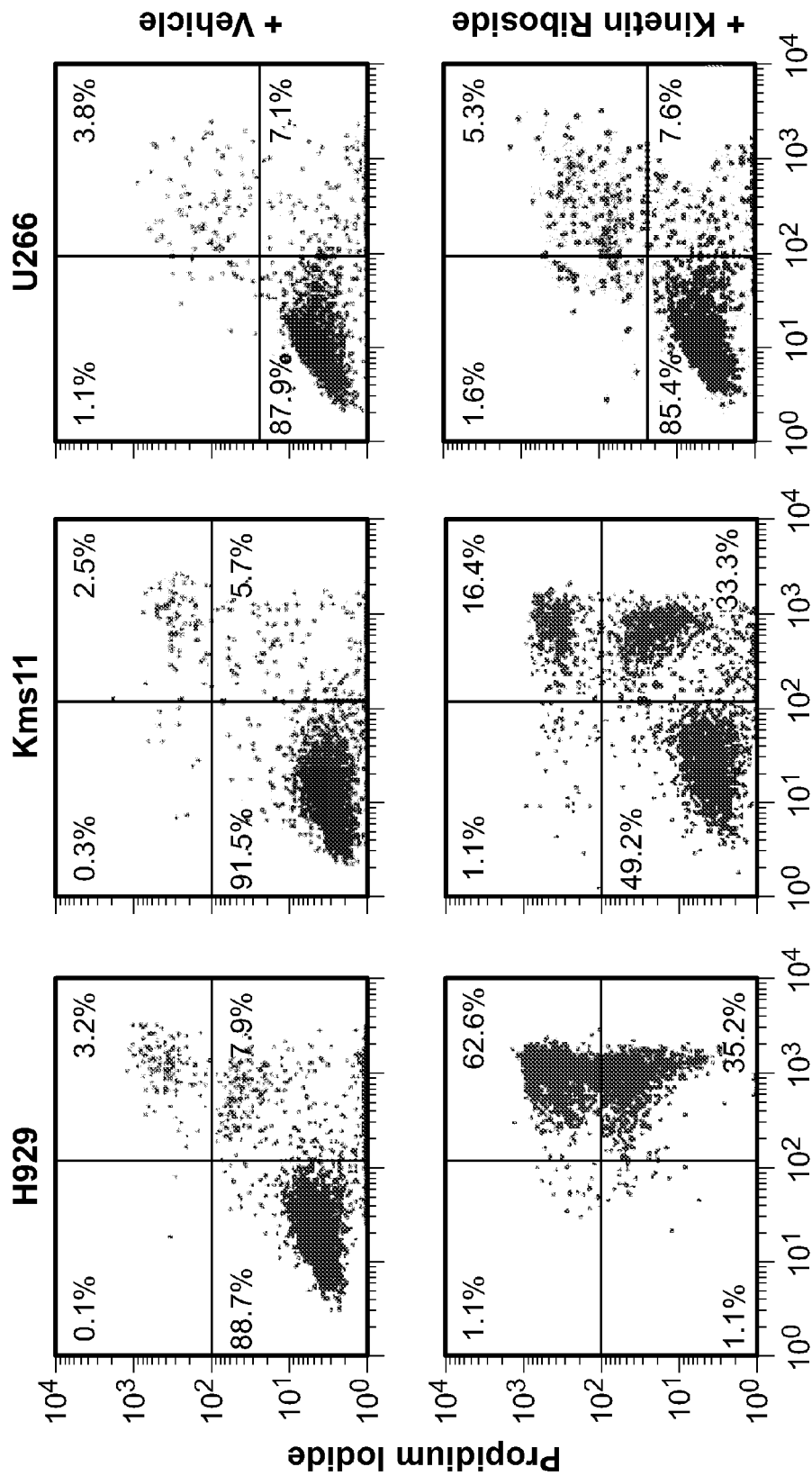
Figure 4D:
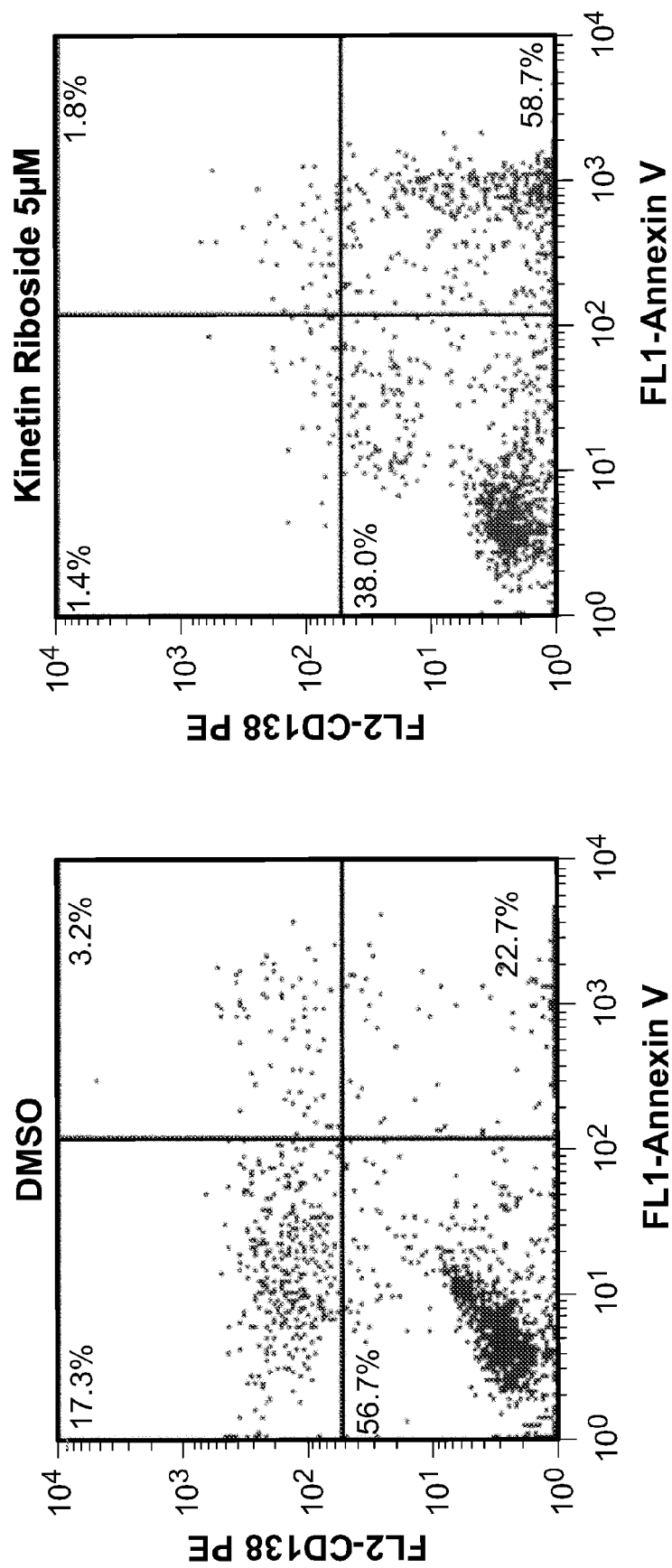

Kinetin riboside induces apoptosis of multiple myeloma cells. Kinetin riboside is cytotoxic to myeloma cell lines (FIG. 4A) with an IC50 of <1.7mg/L (5 µM) in 8 out of 12 HMCL and <5 mg/L (15 µM) in 11/12 HMCL at 48 hours. Cell death is mediated by apoptosis rather than acute injury. Thus, kinetin riboside-treated HMCL (and CD138+ patient myeloma cells) exhibit caspase-9 cleavage by 16 hours (FIG. 2B & FIG. 5), acquisition of Annexin-V surface binding (redistribution of plasma membrane phosphatidylserine) and loss of CD138 expression by 24-96 hours (FIG. 4D). Apoptotic plasma cells lose CD138 expression (Jourdan et al., Br. J. Haematol., 100:637-46 (1998)).

Figure 4E:
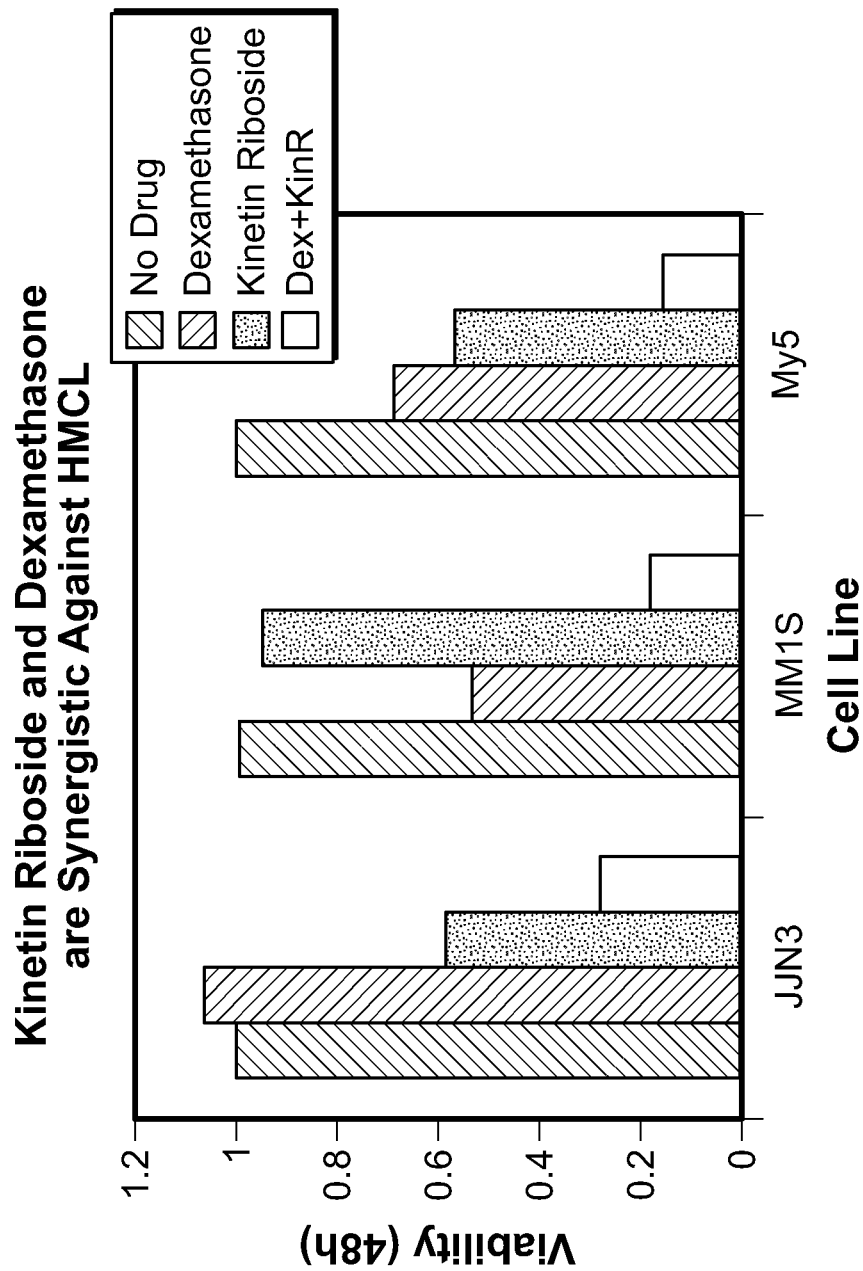

As mouse embryos that lack any D-cyclins eventually die from hematopoietic failure (Kozar et al., Cell, 118, 477-91 (2004)), the bone marrow might be predicted to be one of the most sensitive non-malignant tissue to be affected by drugs targeting cyclin D expression. Unsorted bone marrow samples from myeloma patients were treated with kinetin riboside to assess the relative cytotoxicity of this drug on malignant versus non-malignant marrow cells. Bone marrow samples were first processed to remove non-nucleated red cells and were then treated for 48 hours with kinetin riboside (5 µM). At this concentration kinetin riboside preferentially killed patient CD138+ myeloma cells (92% kill) while leaving the majority of non-malignant CD138− marrow cells intact (FIG. 4E). By comparison, the conventional cytotoxic agent, melphalan, killed proportionately more healthy CD138− marrow cells than malignant myeloma cells in the same assay.

Synergy with glucocorticosteroids. Corticosteroids such as dexamethasone represent one of the most effective treatment options in myeloma. Kinetin riboside was tested together with dexamethasone for additive cytotoxicity against HMCL. Kinetin riboside and dexamethasone act synergistically on HMCL (FIG. 4B). JJN3, for example, is insensitive to low dose dexamethasone and has an IC50 for kinetin riboside of about 5 µM. MM.1S by contrast is partly sensitive to dexamethasone and minimally sensitive to kinetin riboside at these concentrations. Treatment of either cell line with a combination of kinetin riboside and dexamethasone, however resulted in enhanced cytotoxicity that was more than simply additive, indicating that kinetin riboside sensitizes cells to dexamethasone and vice versa. Similarly, while My5 is only weakly responsive to either dexamethasone or kinetin riboside alone, the combination results in marked cytotoxicity.

Kinetin riboside requires adenosine kinase. Kinetin riboside is an adenosine derivative and may therefore enter nucleoside metabolic pathways. A-134974 is a specific inhibitor of adenosine kinase that at low concentrations has no effect on 3T3 cell viability and causes minimal enhancement of CCND2-luc expression (FIG. 5B). However, A-134974 completely inhibits kinetin riboside-induced suppression of CCND2 in 3T3 cells (FIG. 5B) and partially rescues cyclin D1 and D2 levels in kinetin riboside-treated HMCL (FIG. 5A), indicating that kinetin riboside is dependent upon the target enzyme, adenosine kinase, and suggesting that kinetin riboside may require phosphorylation for maximal activity.

Figure 5A:
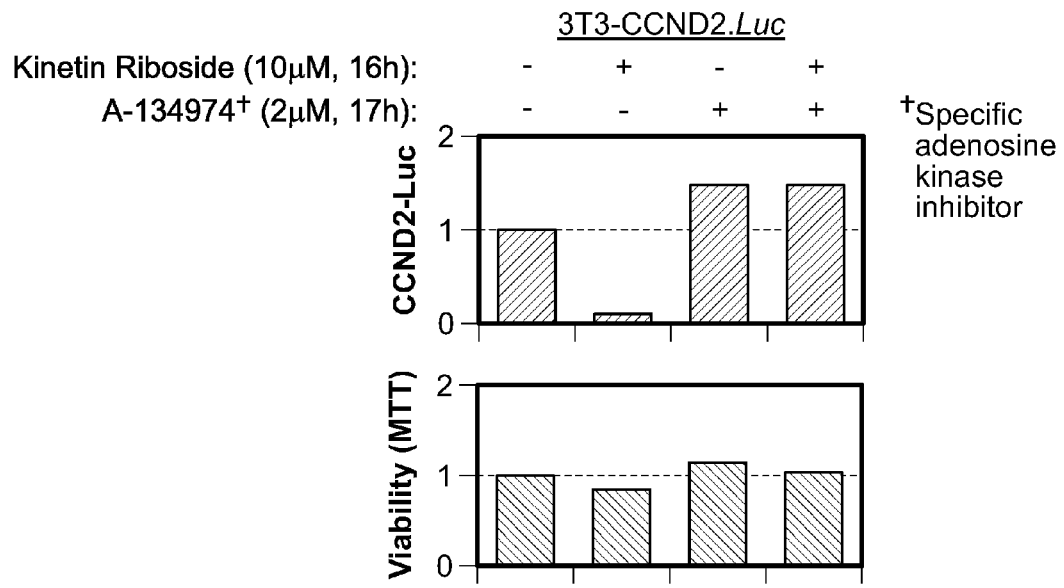
FIG. 5. Kinetin riboside requires adenosine kinase for its activity. (A) Kinetin riboside-induced suppression of CCND2 transactivation in NIH 3T3 cells is abolished by the adenosine kinase inhibitor, A-134974 (2 µM). 3T3 cells containing the CCND2 promoter-luc reporter construct were pre-incubated with A-134974 (2 µM) for 1 hour and were then treated with kinetin riboside (10 µM) for 16 hours; CCND2 transactivation plus viability were determined by luciferase assay and MTS assay respectively. (B) Western blot showing that kinetin riboside (10 µM)-induced cyclin D suppression and caspase 9 cleavage are similarly diminished by A-134974 (2 µM) in HMCL.
Figure 5B:
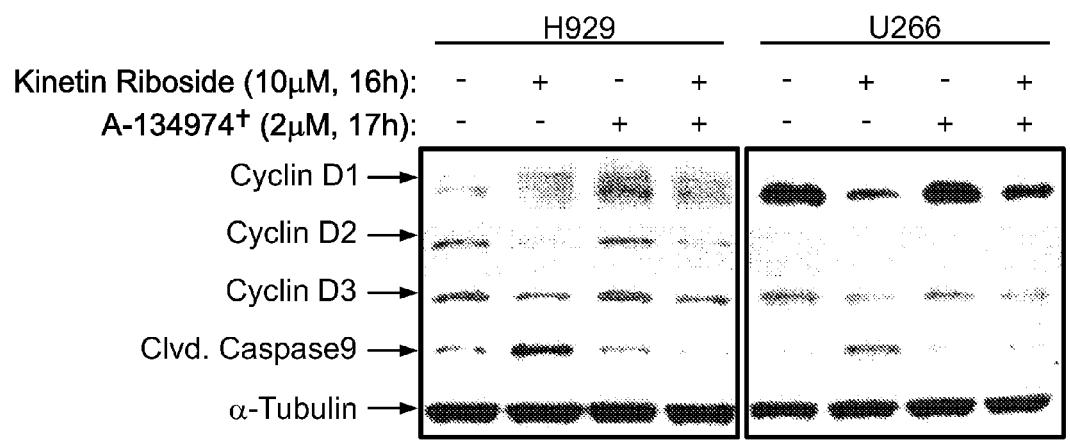

In addition to limiting cyclin D1 or D2 suppression, A-134974 prevents kinetin riboside-induced caspase 9 cleavage in HMCL, an indicator of apoptosis (FIG. 5A). By contrast, S-(4-Nitrobenzyl)-6-thioinosine (NBTI), a potent adenosine uptake inhibitor, does not block kinetin riboside function, indicating that kinetin riboside does not require the adenosine transporter to gain entry into the cell.

Figure 6:
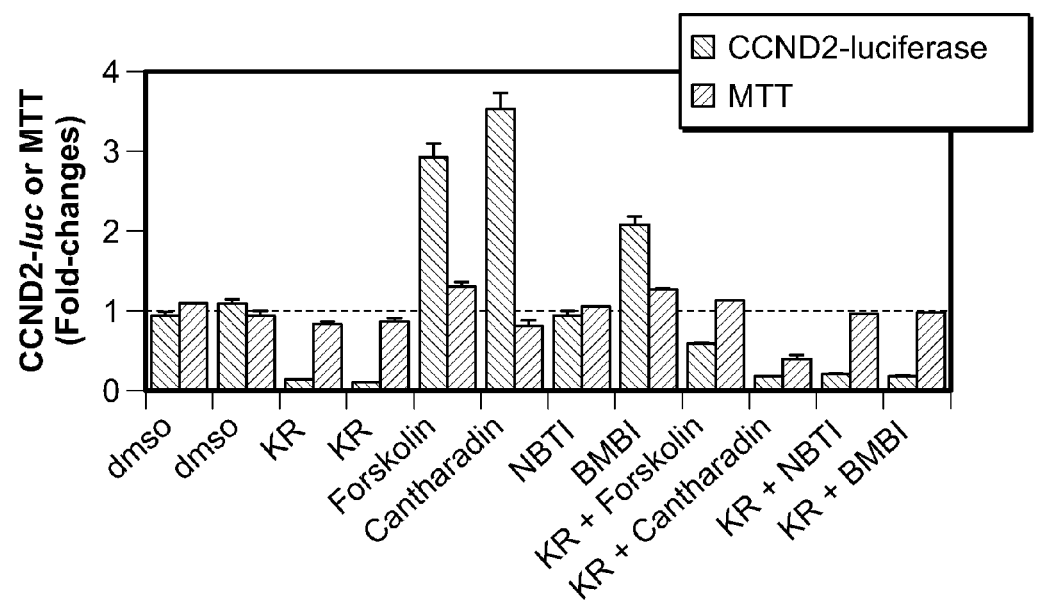
FIG. 6. Kinetin riboside blocks cAMP- and PP2A-induced CCND2 transactivation. NIH 3T3 cells expressing the CCND2 promoter driving luciferase were incubated with kinetin riboside or vehicle control ±forskolin, 4-(3-butoxy-4-methoxybenzyl)imidazolidin-2-one (BMBI), cantharadin, S-(4-Nitrobenzyl)-6-thioinosine (NBTI), or A-134974, as specified at 5 µM concentration for 16 hours at 37° C.; CCND2 transactivation and viability were subsequently assessed as described herein. Forskolin activates adenylate cyclase and BMBI inhibits cAMP phosphodiesterase; both cause an increase in cAMP concentration that can be seen to transactivate CCND2. Cantharadin (C7632) is an inhibitor of protein phosphatase 2A and, similarly, shows induction of CCND2. NBTI is a potent adenosine uptake inhibitor. Kinetin riboside blocks Forskolin and Cantharadin-induced CCND2 transactivation, induced via upregulation of cAMP or the phosphoprotein targets of PP2A. Although a purine analogue, kinetin riboside is unaffected by blockade of cellular adenosine uptake (by NBTI) indicating a distinct cellular uptake mechanism.

Kinetin riboside blocks cAMP- and PP2A-induced CCND2 transactivation. As the cyclic adenosine monophosphate (cAMP)-signaling pathway has a potent transactivating effect on CCND2, whether kinetin riboside acts as an inhibitor of signaling between cAMP and CCND2 was tested. Induction of the cAMP pathway with Forskolin, an activator of adenylate cyclase that causes increased cAMP levels, causes marked transactivation of CCND2 in the 3T3 reporter cells (FIG. 6), and this effect was blocked by co-incubation with kinetin riboside. Similarly, CCND2 transactivation by BMBI, an inhibitor of cAMP phosphodiesterase that also causes increases in cAMP, was also effectively blocked by kinetin riboside, confirming that kinetin riboside does act to block cAMP-induced CCND2 transactivation.

As kinetin riboside blocks cAMP-induced transactivation of CCND2 and is an adenosine derivative that requires adenosine kinase for activity, the hypothesis that kinetin riboside functions as an analog of cAMP was tested. If kinetin riboside functions as an analog of cAMP, it should not affect CCND2 transactivation induced more distally by inhibition of protein phosphatase 2A (PP2A), a negative regulator of the MAP kinase cascade and other cellular protein kinases. Inhibition of PP2A using cantharadin, caused marked transactivation of CCND2, confirming a role for regulatory phosphoproteins in CCND2 control. However, this effect was abolished by kinetin riboside, indicating that this compound blocks CCND2 transactivation at a level that is distal to both cAMP and the phospho-protein targets of PP2A, suggesting that kinetin riboside does not exert its effect simply as a cAMP analog.

Kinetin riboside induces transcriptional repressors hCREM1a/ICER and Bach2. Suppression of CCND2 by kinetin riboside occurs distal to both cAMP and phosphoprotein transactivation signals. In addition, kinetin riboside suppresses cyclin D1 in U266 cells despite cis dysregulation of CCND1 by the IgH enhancer, and suppresses CCND2 in NIH3T3 cells and in JJN3 and Kms11cells, despite transforming overexpression of c-Maf, which directly binds and stimulates the CCND2 promoter. These findings suggest that cyclin D gene suppression induced by kinetin riboside may involve recruitment of a transcriptional repressor to the cyclin D promoter and/or suppression or inactivation of an essential transcription factor. As there is a 4-6 hour lag between kinetin riboside exposure and cyclin D1 or D2 suppression it is surmised that changes in expression of an upstream gene may be required to effect cyclin D gene suppression. Thus, gene expression profiling was used at this time point to assess for potential kinetin riboside effector molecules.

The HMCL, U266, is relatively resistant to kinetin riboside with an IC50>20 µM. While cyclin D1 levels are significantly suppressed by kinetin riboside in this cell line, subsequent apoptosis occurs at only low levels. Gene expression profiling (GEP) was performed on U266 and the fully kinetin riboside-sensitive cell line, H929, 4 hours after treatment with kinetin riboside 5 µM, to mine for early kinetin riboside responsive genes that mediate the kinetin riboside-induced block to CCND1 or CCND2 transactivation common to both cell lines.

Figure 7A:
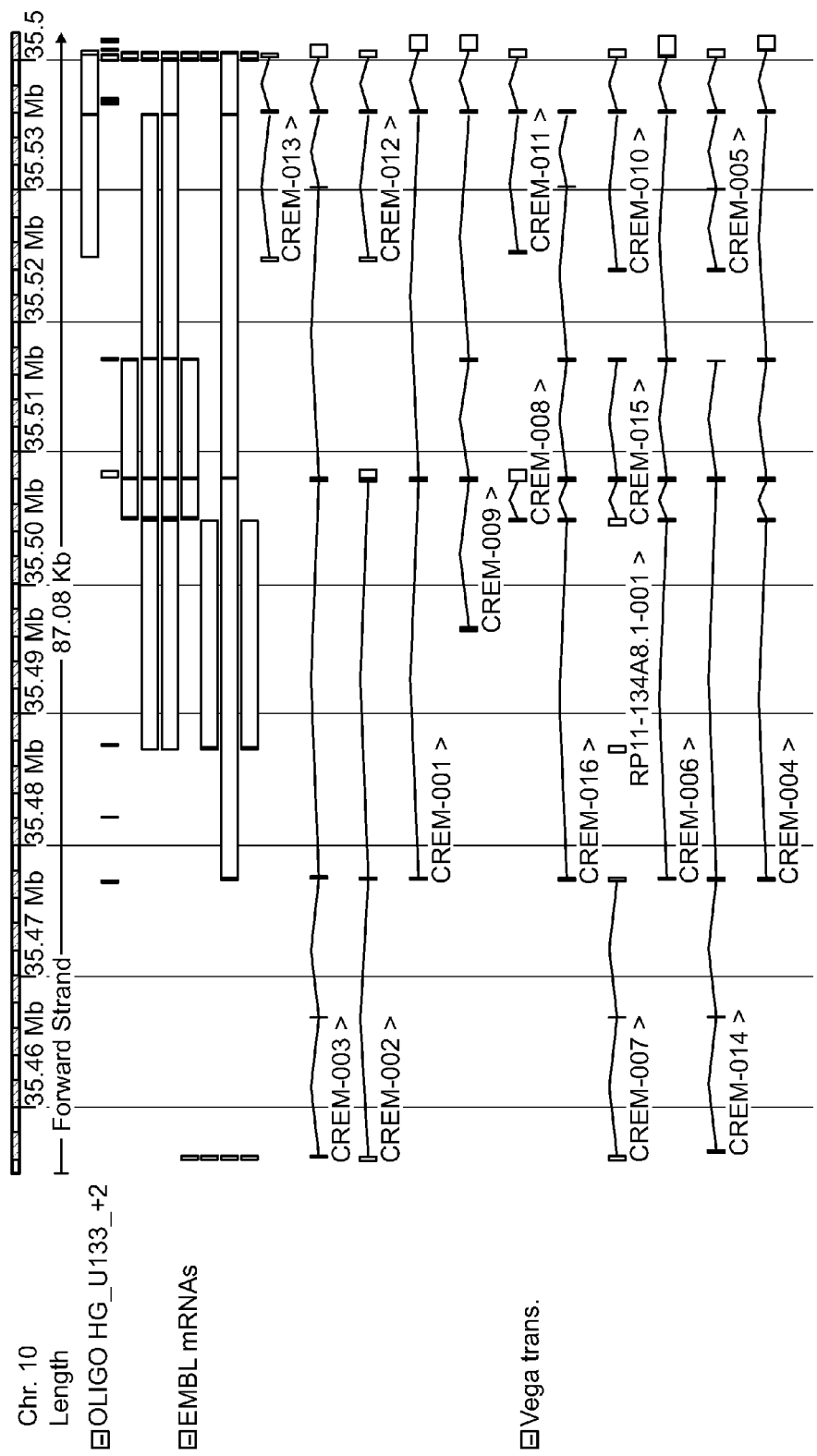
FIG. 7. Transcriptional repressor isoforms of the cyclic AMP response element modulator (CREM) gene, but not activator isoforms, are induced by kinetin riboside. (A) Ensembl human contig map of the CREM gene, variant mRNA transcripts and CREM-specific Affymetrix U133_+2 probe sets. (B) Relative expression levels of CREM 3'UTR- or exon-specific affymetrix probe-sets in H929 or U266 cells 4 hours after treatment with kinetin riboside, pristimerin, or DMSO vehicle. Three CREM probes that show increased expression of a specific CREM isoform(s) in both H929 and U266 cells after kinetin riboside treatment are indicated with a star (*). (C) Correlation of kinetin riboside-induced Affymetrix probe-sets (expression normalized by cell line to DMSO-treated samples) with variant CREM transcripts. (D) List of CREM transcript variants that account for Affymetrix CREM gene expression profile changes induced by kinetin riboside; all are repressors of the cAMP response element (CRE).
Figure 7B:
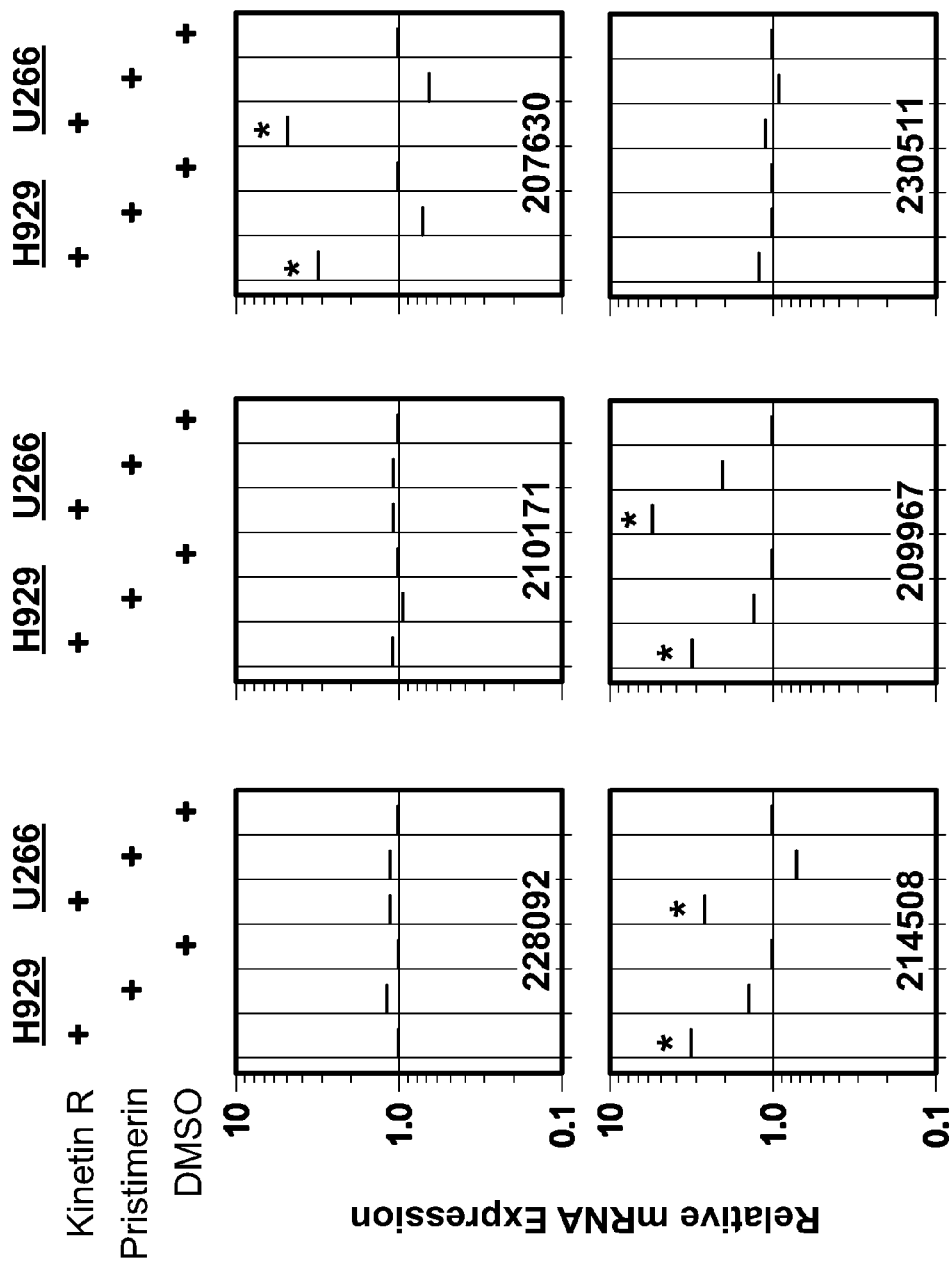
Figure 8:
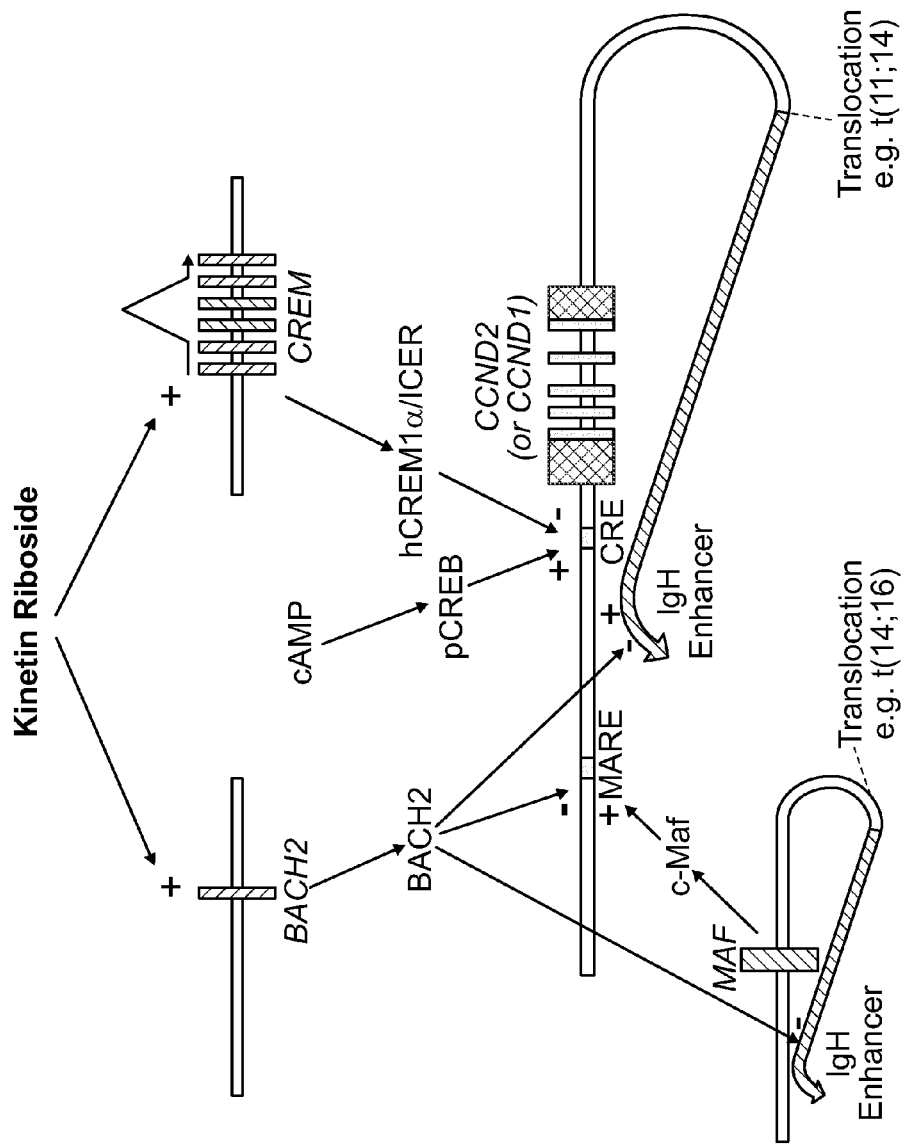
FIG. 8. Hypothetical model of repression of CCND2 and CCND1 by kinetin riboside in myeloma. Transcriptional repressors CREM and BACH2 are rapidly induced by kinetin riboside (<4 hours) and are predicted to block the cAMP-response element (CRE) (common to both CCND 1 and CCND2 (but not CCND3), located immediately 5' to the transcription initiation site) and Maf response elements (MARE), respectively. In addition, Bach2 is a known suppressor of IgH enhancer function and may directly block cyclin D gene expression when this is driven by a translocation to the IgH enhancer locus. In addition, Bach2 upregulation may block cyclin D gene expression when this is transactivated by upstream dysregulation of MAF or FGFR3 (both are dysregulated as the result of translocation of those genes to the IgH enhancer locus).
Figure 10A:
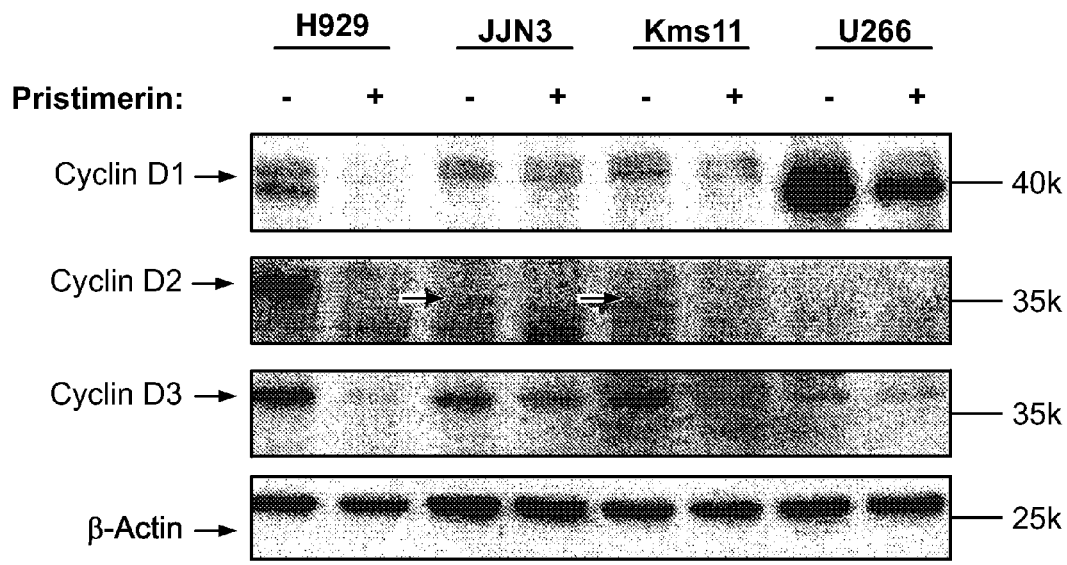
FIG. 10. Suppression of cyclin D1+D2+D3 and induction of caspase cleavage (apoptosis) by Prisitmerin. (A) Western blots showing suppressive effects of pristimerin 0.5 µM at 16 hours on cyclin D protein levels in human myeloma cell lines (HMCL). (B) Time course of cyclin D suppression and caspase activation in the myeloma cell line H929 following pristimerin 0.5 µM exposure. Caspase cleavage is induced from 2-6 hours after treatment and cyclin D proteins are suppressed by 6 hours.
Figure 10B:
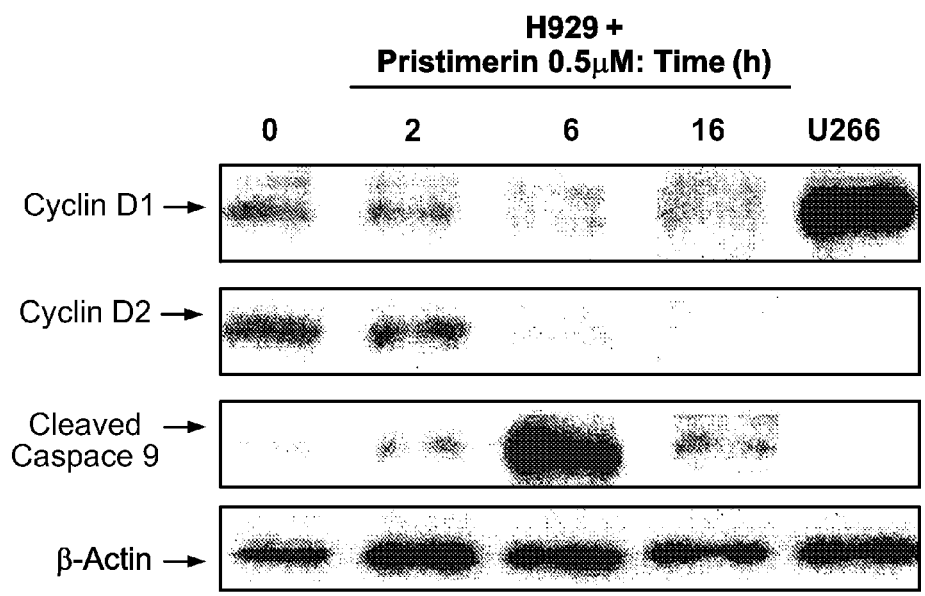
Figure 11A:
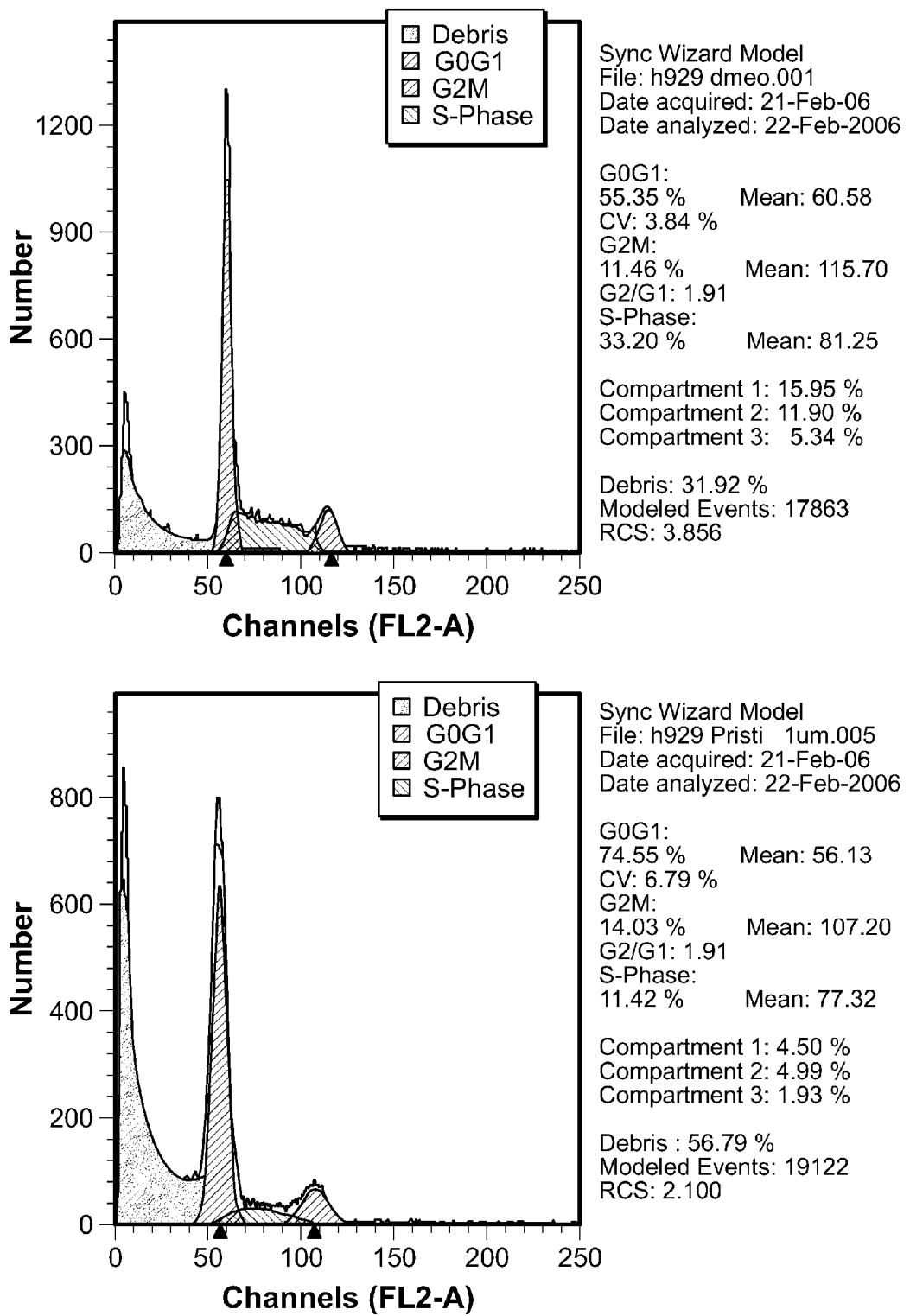
FIG. 11. Pristimerin causes cell cycle arrest (at $G_0/G_1$, preventing S-phase entry) and induces apoptosis in HMCL. Effect of DMSO vehicle or pristimerin 0.5 µM on the cell cycle profiles of (A) H929 and (B) U266 HMCL at 20 hours. Red peaks represent $G_0/G_1$ phase (left) 2N ploidy (both cell lines are hypodiploid) and $G_2/M$ phase (right) 4N ploidy; diagonal shading represents intermediate DNA content corresponding to S-phase. Light blue populations left of G0/G1 represent a sub-G0 apoptotic fraction (with DNA fragmentation) and cellular debris (far left peak).
Figure 11B:
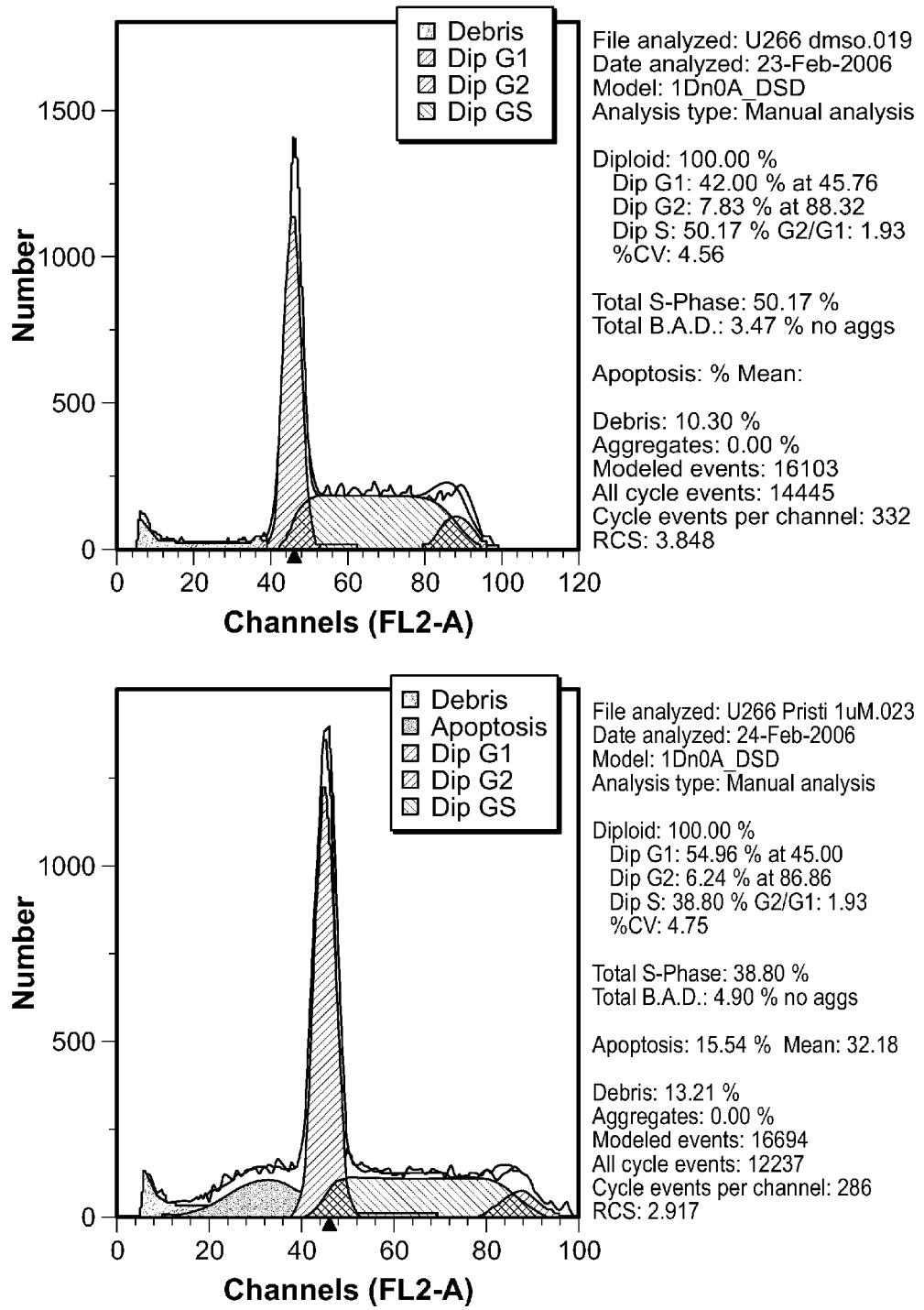

At 4 hours kinetin riboside induced a 3-fold or greater change in the expression of approximately 35 genes in both H929 and U266 cells (Table 1). Notably, given the potency of cAMP pathway signaling on CCND2 transactivation, kinetin riboside induced rapid expression of the cAMP response element (CRE) modulator (CREM) gene. CREM encodes bZIP transcription factors that bind the cAMP responsive element (CRE) found in many gene promoters. From alternative promoter and translation initiation sites CREM encodes numerous transcript splice variants (FIG. 7A), providing temporal and tissue specificity to cAMP responsiveness. CREM isoforms function either as activators or repressors of CRE-mediated transcription. Kinetin riboside caused preferential induction of CREM isoforms, all of which function as CRE repressors, but failed to induce CRE activator isoforms (FIG. 7B-D), thereby providing a nuclear block to the expression of select cAMP responsive genes, including CCND2 and CCND 1. CCDN2 has been shown to be responsive to CREM repressor control. Evolutionarily conserved CRE plus ATF/E4F/AP1(or cJun) multi-transcription factor binding sites are present in both CCND2 and CCND1 promoters immediately 5' (<50 bp) from the start of transcription (5' UTR) but are absent in the evolutionary conserved CCND3 5' regulatory region, providing a mechanism for the observed specificity in cyclin D response to kinetin riboside.

TABLE 1

HMCL gene expression changes after kinetin riboside treatment. Genes whose expression was increased or decreased by a factor of ≥3 in both H929 and U266 by kinetin riboside (5 µM, 4 hours).

| Probe | Fold change | Gene | Name |
| --- | --- | --- | --- |
| 221641_s_at | 3.4 | ACATE2 | likely ortholog of mouse acyl-Coenzyme A thioesterase 2, mitochondrial |
| 239277_at | 3.3 | ACATE2 | likely ortholog of mouse acyl-Coenzyme A thioesterase 2, mitochondrial |
| 212543_at | 7.2 | AIM1 | absent in melanoma 1 (putative melanoma tumor suppressor) |
| 208836_at | 3.2 | ATP1B3 | ATPase, Na+/K+ transporting, beta 3 polypeptide |
| 218631_at | 5.7 | AVPI1 | vasopressin-induced transcript |
| 228498_at | 5.2 | B4GALT1 | UDP-Gal:betaGlcNAc beta 1,4-galactosyltransferase, polypeptide 1 |
| 221234_s_at | 15.1 | BACH2 | BTB and CNC homology 1, basic leucine zipper transcription factor 2 |
| 210785_s_at | 7.0 | C1orf38 | chromosome 1 open reading frame 38 |
| 207571_x_at | 6.9 | C1orf38 | chromosome 1 open reading frame 38 |
| 224836_at | 4.3 | C20orf110 | chromosome 20 open reading frame 110 |
| 204637_at | 34.4 | CGA | glycoprotein hormones, alpha polypeptide |
| 217783_s_at | 5.0 | CGI-127 | yippee protein (conserved in all eukaryotes with putative role in cell division) |
| 222408_s_at | 4.6 | CGI-127 | yippee protein |
| 207630_s_at | 3.2 | CREM | cAMP responsive element modulator |
| 209967_s_at | 3.1 | CREM | cAMP responsive element modulator |
| 206085_s_at | 5.3 | CTH | cystathionase (cystathionine gamma-lyase) |
| 217127_at | 5.0 | CTH | cystathionase (cystathionine gamma-lyase) |
| 1555950_a_at | 7.9 | DAF | UI-H-EI0-ayo-p-15-0-UI.s1 NCI_CGAP_EI0 Homo sapiens cDNA clone UI-H-EI0-ayo-p-15-0-UI 3', mRNA sequence. |
| 204015_s_at | 13.8 | DUSP4 | dual specificity phosphatase 4 |
| 204014_at | 7.9 | DUSP4 | dual specificity phosphatase 4 |
| 228188_at | 13.9 | FOSL2 | FOS-like antigen 2 (FosL2, Fra2) |
| 218880_at | 7.8 | FOSL2 | FOS-like antigen 2 |
| 225262_at | 4.9 | FOSL2 | FOS-like antigen 2 |
| 218881_s_at | 4.0 | FOSL2 | FOS-like antigen 2 |
| 205409_at | 3.9 | FOSL2 | FOS-like antigen 2 |
| 203397_s_at | 9.5 | GALNT3 | UDP-N-acetyl-alpha-D-galactosamine:polypeptide N-acetylgalactosaminyltransferase 3 (GalNAc-T3) |
| 214430_at | 3.1 | GLA | galactosidase, alpha |
| 227539_at | 7.3 | GNA13 | guanine nucleotide binding protein (G protein), alpha 13 |
| 202814_s_at | 4.2 | HIS1 | HMBA-inducible |
| 213793_s_at | 3.9 | HOMER1 | homer homolog 1 (Drosophila) |

TABLE 1-continued

HMCL gene expression changes after kinetin riboside treatment. Genes whose expression was increased or decreased by a factor of ≥3 in both H929 and U266 by kinetin riboside (5 µM, 4 hours).

| Probe | Fold change | Gene | Name |
|---|---|---|---|
| 226651_at | 3.4 | HOMER1 | homer homolog 1 (*Drosophila*) |
| 241985_at | 15.3 | JMY | junction-mediating and regulatory protein |
| 226352_at | 4.2 | JMY | junction-mediating and regulatory protein |
| 201751_at | 4.6 | KIAA0063 | KIAA0063 gene product |
| 212733_at | 3.5 | KIAA0226 | KIAA0226 gene product |
| 212503_s_at | 3.9 | KIAA0934 | KIAA0934 protein |
| 219371_s_at | 0.2 | KLF2 | Kruppel-like factor 2 (lung) |
| 222068_s_at | 17.3 | LOC123872 | similar to RIKEN cDNA 4930457P18 |
| 202340_x_at | 7.3 | NR4A1 | nuclear receptor subfamily 4, group A, member 1 (NuR77) |
| 207978_s_at | 12.7 | NR4A3 | nuclear receptor subfamily 4, group A, member 3 |
| 209959_at | 11.4 | NR4A3 | Human mitogen induced nuclear orphan receptor (MINOR) mRNA, complete cds. |
| 217739_s_at | 6.5 | PBEF1 | pre-B-cell colony enhancing factor 1 |
| 1555167_s_at | 6.5 | PBEF1 | pre-B-cell colony enhancing factor 1 |
| 238592_at | 6.0 | PDLIM3 | PDZ and LIM domain 3 |
| 209621_s_at | 5.8 | PDLIM3 | PDZ and LIM domain 3 |
| 210170_at | 5.5 | PDLIM3 | PDZ and LIM domain 3 |
| 218319_at | 7.1 | PELI1 | pellino homolog 1 (*Drosophila*) |
| 202388_at | 10.2 | RGS2 | regulator of G-protein signalling 2, 24 kDa |
| 212099_at | 5.2 | RHOB | ras homolog gene family, member B |
| 1553962_s_at | 5.2 | RHOB | 603295907F1 NIH_MGC_96 *Homo sapiens* cDNA clone IMAGE: 5315136 5', mRNA sequence. |
| 210592_s_at | 23.8 | SAT | spermidine/spermine N1-acetyltransferase |
| 203455_s_at | 20.9 | SAT | spermidine/spermine N1-acetyltransferase |
| 213988_s_at | 16.6 | SAT | spermidine/spermine N1-acetyltransferase |
| 230333_at | 9.5 | SAT | spermidine/spermine N1-acetyltransferase |
| 218872_at | 6.5 | TSC | hypothetical protein FLJ20607 |
| 204141_at | 6.2 | TUBB | tubulin, beta polypeptide |
| 208622_s_at | 4.7 | VIL2 | villin 2 (ezrin) |
| 210561_s_at | 3.2 | WSB1 | WD repeat and SOCS box-containing 1 |
| 226034_at | 9.1 | | Clone IMAGE: 3881549, mRNA |
| 227200_at | 4.3 | | Transcribed sequences |

By gene expression profiling, kinetin riboside also induced expression of the transcription factor Fos-like antigen 2 (FosL2) and the transcription repressor BACH2 (BTB and CNC homology 1, basic leucine zipper transcription factor 2). While isolated induction of FosL2 might be expected to promote transcription of CCND1 or CCND2, BACH2 functions as a repressor of Ap-1 and Maf sites and may counteract FosL2, possibly contributing to kinetin riboside-induced cyclin D gene suppression. In addition, induction of CREM repressor(s), that bind the distal cyclin D2 (±D1) gene promoters at the start of transcription, may act to block any effects of FosL2 on CCND2 or D1 transcription.

Kinetin riboside toxicity in mice. In vivo toxicity studies of synthetic kinetin riboside were initiated in balc/c mice. Existing data on kinetin riboside activity in mice is based upon 'aqueous solutions' of kinetin riboside, although this drug has limited aqueous solubility at high concentration. From preliminary studies, the maximum tolerated single dose (MTDs) of kinetin riboside in mice was found to be about 25 mg/kg by intravenous (IV) route or 100 mg/kg by intraperitoneal (IP) route. At these concentrations, mice exhibited hypoactivity for 15-30 minutes after treatment but recover without long-term effects. A multi-dose regimen of kinetin riboside 80 mg/kg IP daily×30 days is also well tolerated, with no overt toxicity, and no vital organ pathology by histology section on day 8, three days after treatment completion. A dose of 25 mg/kg equates to a final concentration of about 60 µM (i.e., 12× the $IC_{50}$ of kinetin riboside for myeloma cell lines) if the volume of distribution is taken to be the weight of the mouse. The actual volume of distribution and the half-life of kinetin riboside in vivo are at present unknown and future schedules of administration may require adjustment to account for these.

Example 3

Kinetin Riboside Inhibits Growth of Human Myeloma Xenograft Tumors

Female nude X-linked immune-deficient (BNX) mice purchased from NCI-Frederick were used for in vivo studies. Animals had access to food and water ad libitum and were handled in accordance with animal care and use guidelines. Eight-week-old mice were inoculated with My5 or 8226 ($2 \times 10^7$) MM cells subcutaneously (s.c.) in the right flank. Kinetin riboside (pre-dissolved in DMSO at 500 mg/mL and stored at −20° C.) was formulated daily by dropwise dissolution to 3.7 mg/mL in pre-warmed (37° C.) 0.9% saline, 1% β2-hydroxypropylcyclodextrin (Sigma) solution and was administered 1×-5× daily at 85 mg/kg/dose. The first dose daily was given intraperitoneally and remaining doses were given s.c. with increasing dosing intervals (30, 60, 120, 180 minutes). Tumor volumes were measured using vernier calipers and calculated with the formula L×W×H×2/3. P-values were calculated by paired t-test (JMP 6.0, SAS; Cary, N.C.).

Figure 14B:
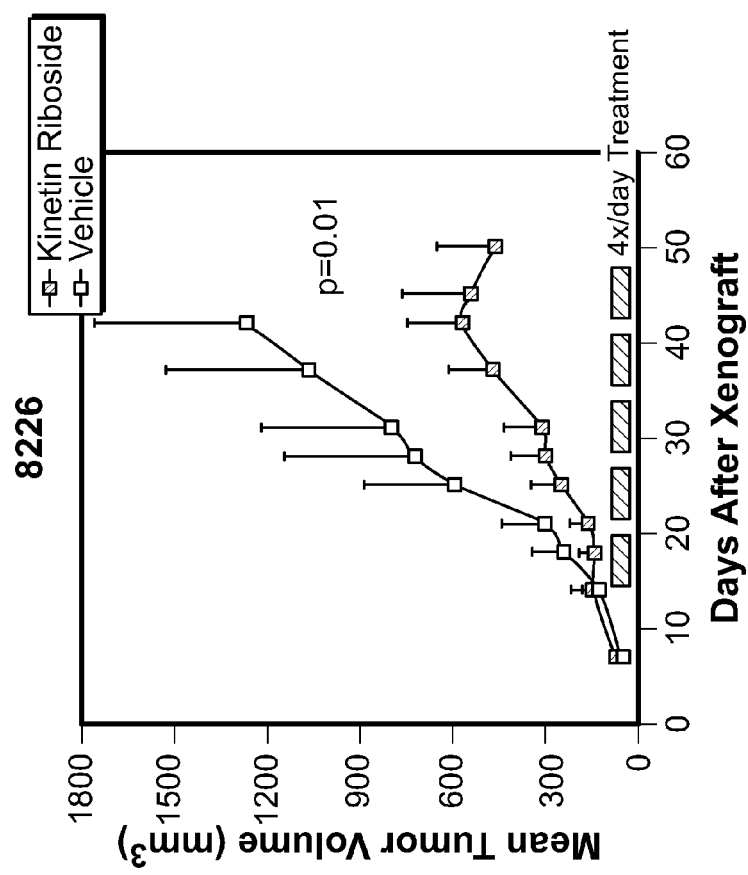
FIG. 14. Kinetin riboside induces tumor growth arrest in My5 and 8226 myeloma tumor xenografts. (A) Matched pairs of nude mice bearing My5 tumors were treated intra-peritoneally (i.p.) with vehicle control (□) or with kinetin riboside (■) at escalating dose-density from 100 mg/kg once daily to 85mg/kg 5×/daily, administered 5 days per week, commencing after mean tumor volume reached 135mm$^3$. Mean tumor volumes±SEM are shown from the time of xenografting (n=4/group). (B) Nude mice bearing 8226 tumors were treated with vehicle (□) or with kinetin riboside (■) (n=4/group), commencing at 85 mg/kg QID (i.p. and s.c.) when the mean tumor volume exceeded 135 mm$^3$.
Figure 14A:
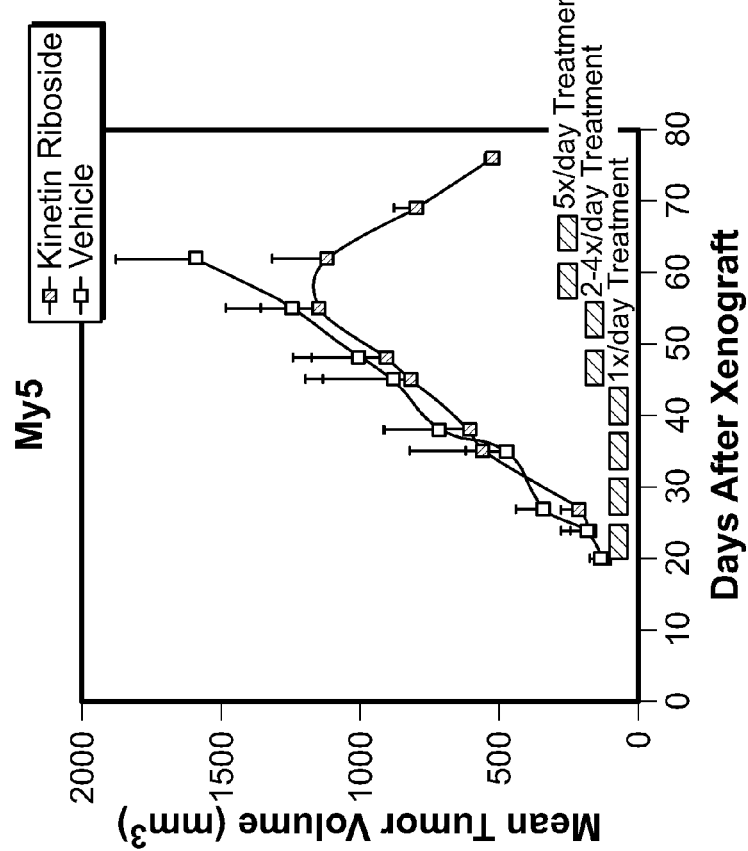

The anti-tumor activity of kinetin riboside in vivo was evaluated against My5 and 8226 human myeloma tumors grown as xenografts in nude mice. Drug or vehicle were initially administered once daily with dosing up to 100 mg/kg/day, however, no effect on 8226 or My5 (FIG. 14A) tumor growth was observed. Nevertheless, as the limiting toxicity for single-dose escalation was transient mild sedation with short duration ($t_{1/2}$ about 15 minutes), an intensified multi-dosing regimen was subsequently instituted to counter rapid drug redistribution or clearance. Consistent with a short drug half-life, rapidly repeated doses of kinetin riboside (up to five per day at 85 mg/kg/dose) were well tolerated. Moreover, with progressive dose-density intensification in My5-xenografted mice, tumor stasis was observed at 4× daily dosing, and regression of tumors was observed at 5× daily dosing, despite substantial preceeding tumor growth (FIG. 14A). Xenograft studies were then repeated with 8226 tumors using kinetin riboside 85 mg/kg 4× daily upfront, started when tumors had reached a mean volume of 135 mm$^3$ (FIG. 14B). Statistically significant tumor growth inhibition was demonstrated compared to vehicle-treated mice (p<0.01). No effects on neutrophil counts (at 14 days treatment) or on body weight were observed.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating a mammal having multiple myeloma, wherein said method comprises administering kinetin riboside and a glucocorticosteroid to said mammal.

2. The method of claim 1, wherein said mammal is a human.

3. The method of claim 1, wherein said glucocorticosteroid is dexamethasone.

4. A method treating multiple myeloma in a mammal, wherein said method comprises:
    (a) identifying a mammal having multiple myeloma and in need of reduced cyclin D polypeptide activity, and
    (b) administering an agent to said mammal having multiple myeloma, wherein said agent is β-lapachone, dihydrogambogic acid, pristimerin, kinetin riboside, or a combination thereof.

5. The method of claim 4, wherein said mammal is a human.

6. The method of claim 4, wherein said agent is kinetin riboside.

7. The method of claim 4, wherein said agent is dihydrogambogic acid.

8. The method of claim 4, wherein said agent is pristimerin.

9. The method of claim 4, wherein said method comprises administering kinetin riboside and a glucocorticosteroid to said mammal.

10. The method of claim 9, wherein said glucocorticosteroid is dexamethasone.

* * * * *